US008894623B2

(12) United States Patent
Romano

(10) Patent No.: US 8,894,623 B2
(45) Date of Patent: *Nov. 25, 2014

(54) STERILE LIQUID MATERIALS DISTRIBUTION, CONSUMPTION AND MATERIAL WASTE DISPOSAL METHOD AND APPARATUS

(75) Inventor: Jack W. Romano, Kirkland, WA (US)

(73) Assignee: Medindica-Pak, Inc, Kirkland, WA (US)

( * ) Notice: Subject to any disclaimer, the term of this patent is extended or adjusted under 35 U.S.C. 154(b) by 549 days.

This patent is subject to a terminal disclaimer.

(21) Appl. No.: 12/932,104

(22) Filed: Feb. 17, 2011

(65) Prior Publication Data
US 2011/0172613 A1      Jul. 14, 2011

Related U.S. Application Data

(63) Continuation of application No. 10/280,731, filed on Oct. 26, 2002, now Pat. No. 7,931,629.

(60) Provisional application No. 60/346,416, filed on Nov. 1, 2001.

(51) Int. Cl.
*A61M 1/00* (2006.01)

(52) U.S. Cl.
CPC .................. *A61M 1/0001* (2013.01)
USPC ............ 604/319; 604/403; 604/540; 206/438

(58) Field of Classification Search
USPC .......... 604/313, 317, 319, 403; 206/216, 438, 206/570; 222/92, 129
See application file for complete search history.

(56) References Cited

U.S. PATENT DOCUMENTS

| 5,586,973 | A  | * | 12/1996 | Lemaire et al. ................. 604/19 |
| 6,492,332 | B1 | * | 12/2002 | Demopulos et al. ......... 514/17.4 |
| 6,942,123 | B2 |   | 9/2005  | Wertenberger |
| 2004/0149348 | A1 | | 8/2004  | Wertenberger |
| 2009/0057347 | A1 | | 3/2009  | Leys |

\* cited by examiner

*Primary Examiner* — Melanie Hand

(57) ABSTRACT

The present invention is directed towards a method and apparatus for packaging or containing, handling and managing of a variety of materials or other contents from a variety of sources which encounter use under various dynamic applications, conditions and for a plurality of purposes. The invention more specifically is directed towards one or more containers or packages, suitably fitted or used for the handling or managing of materials or other contents along one or more cycles or chains of use. The one or more packages or other containers described herein are intended for and/or used in one or more interconnections or associations with not only the "initial purpose" filling, transport, storage, dispensing, pouring, using, releasing of sterile or other fluids or material contents, but also used in association with, and for carrying out, the additional delivering and receiving of said fluids or materials, and receiving and delivering of said fluids or materials via an ingress and egress, by a variety of ways, for a variety of functions and for a plurality of purposes.

20 Claims, 17 Drawing Sheets

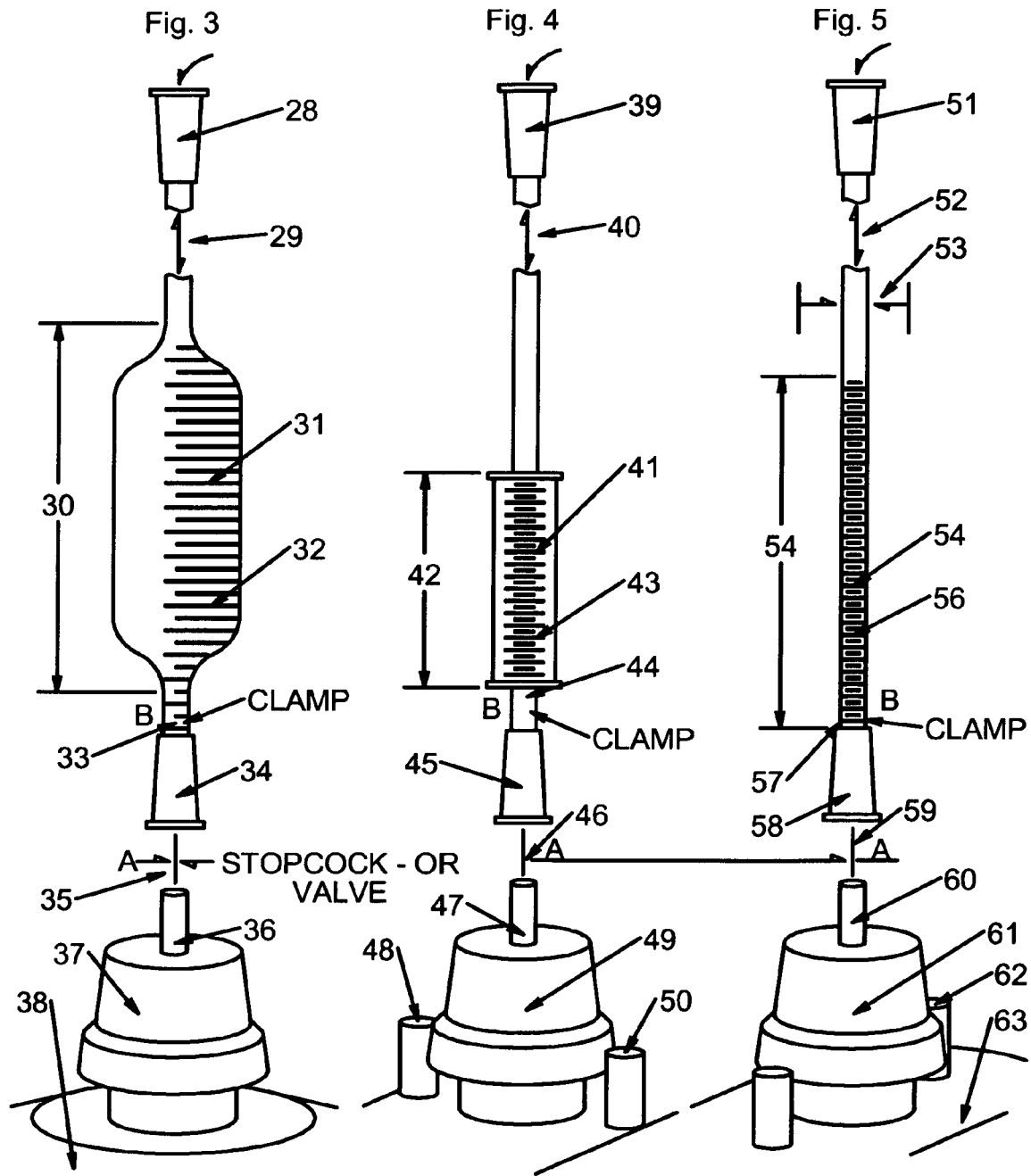

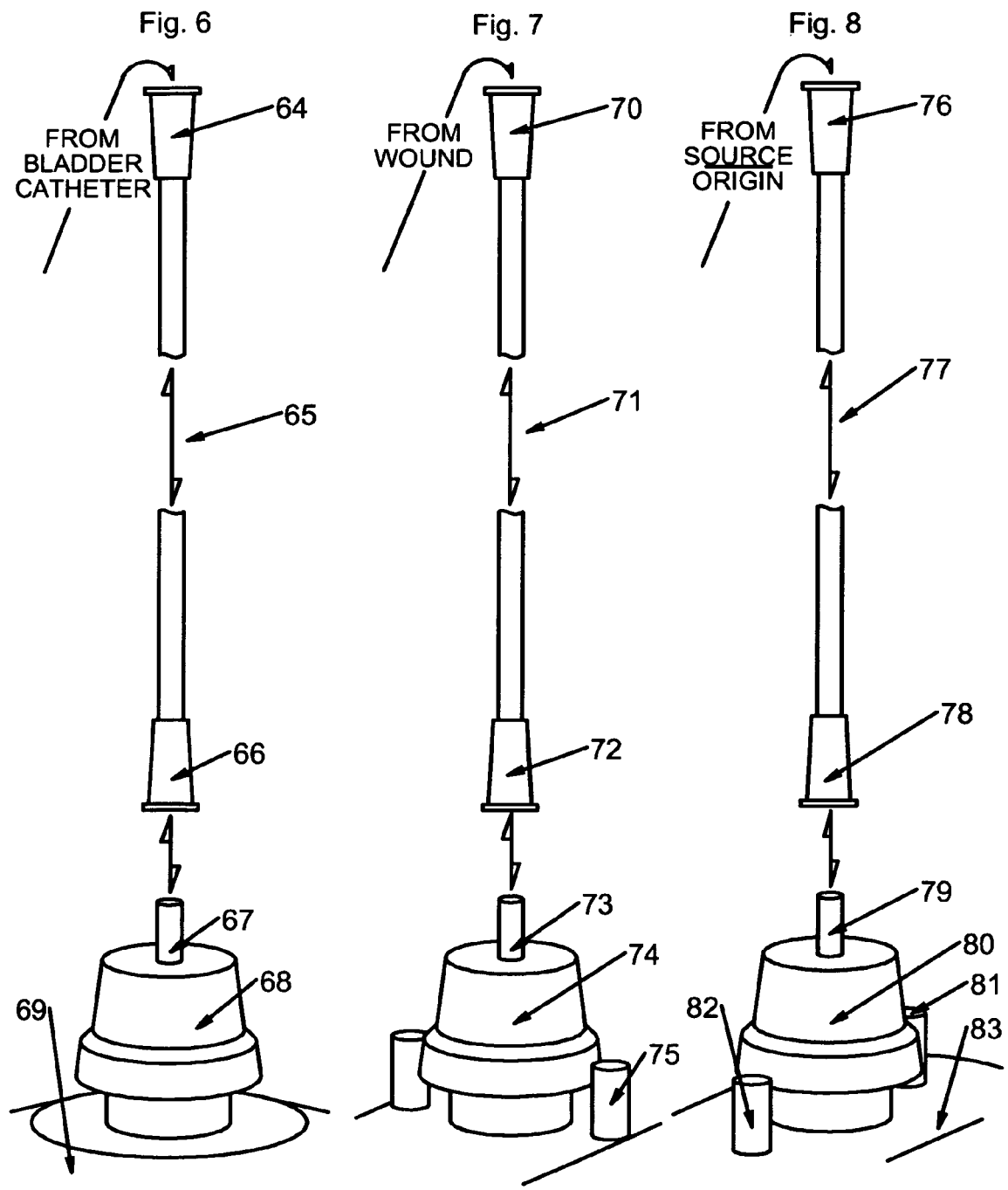

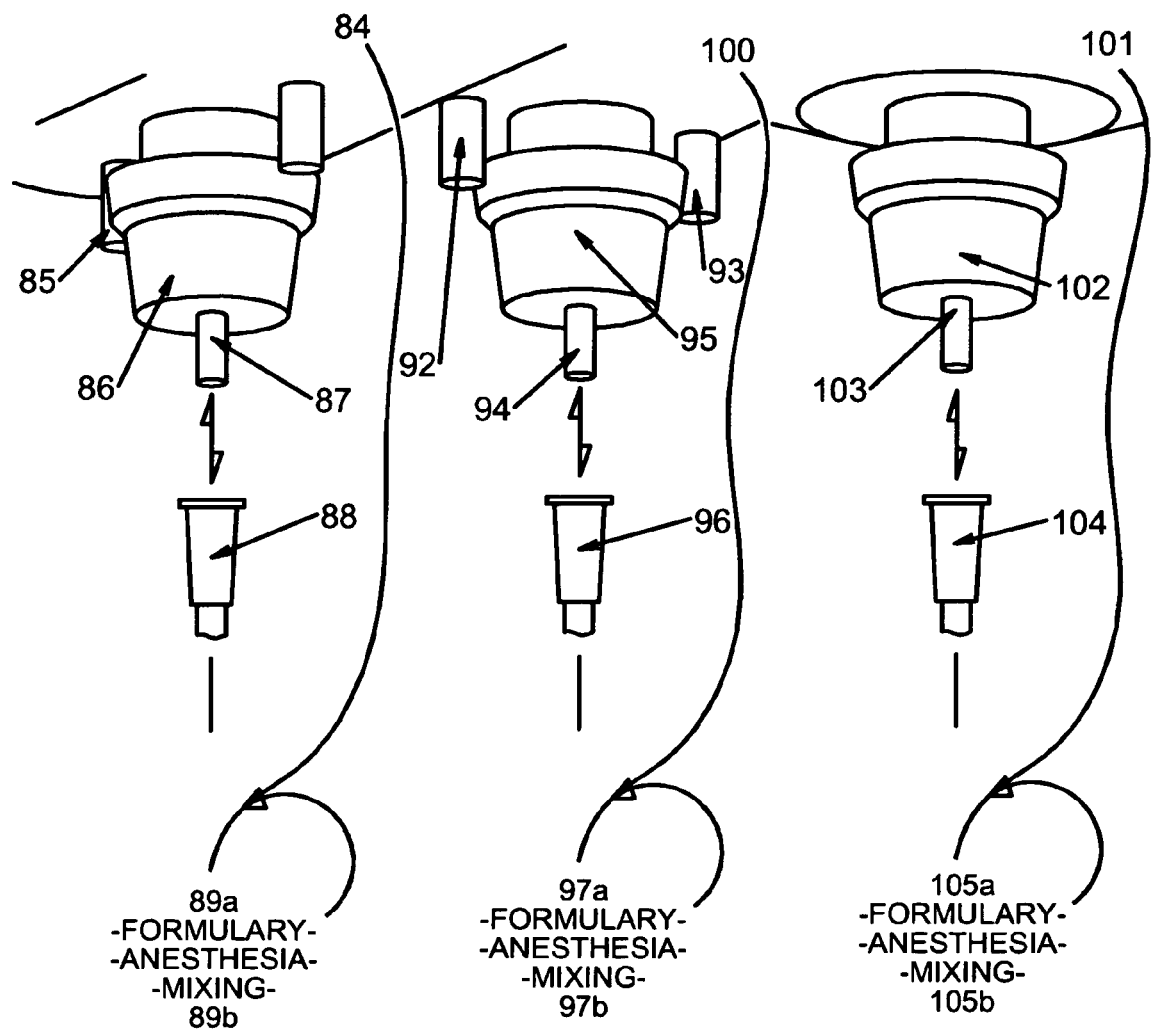
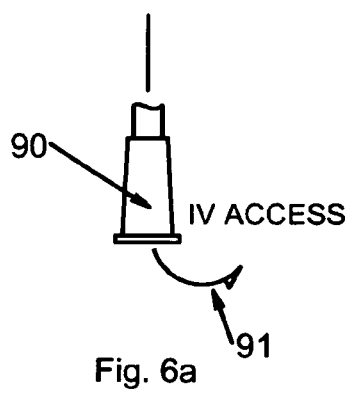
Fig. 6a
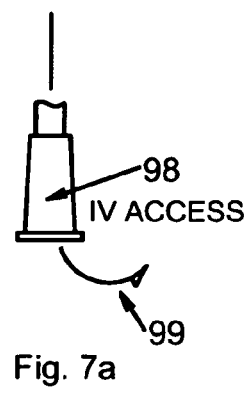
Fig. 7a
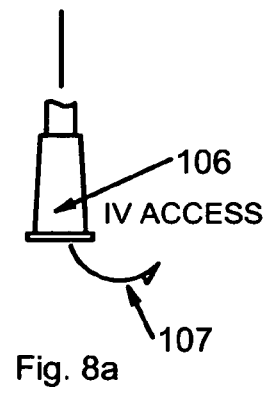
Fig. 8a

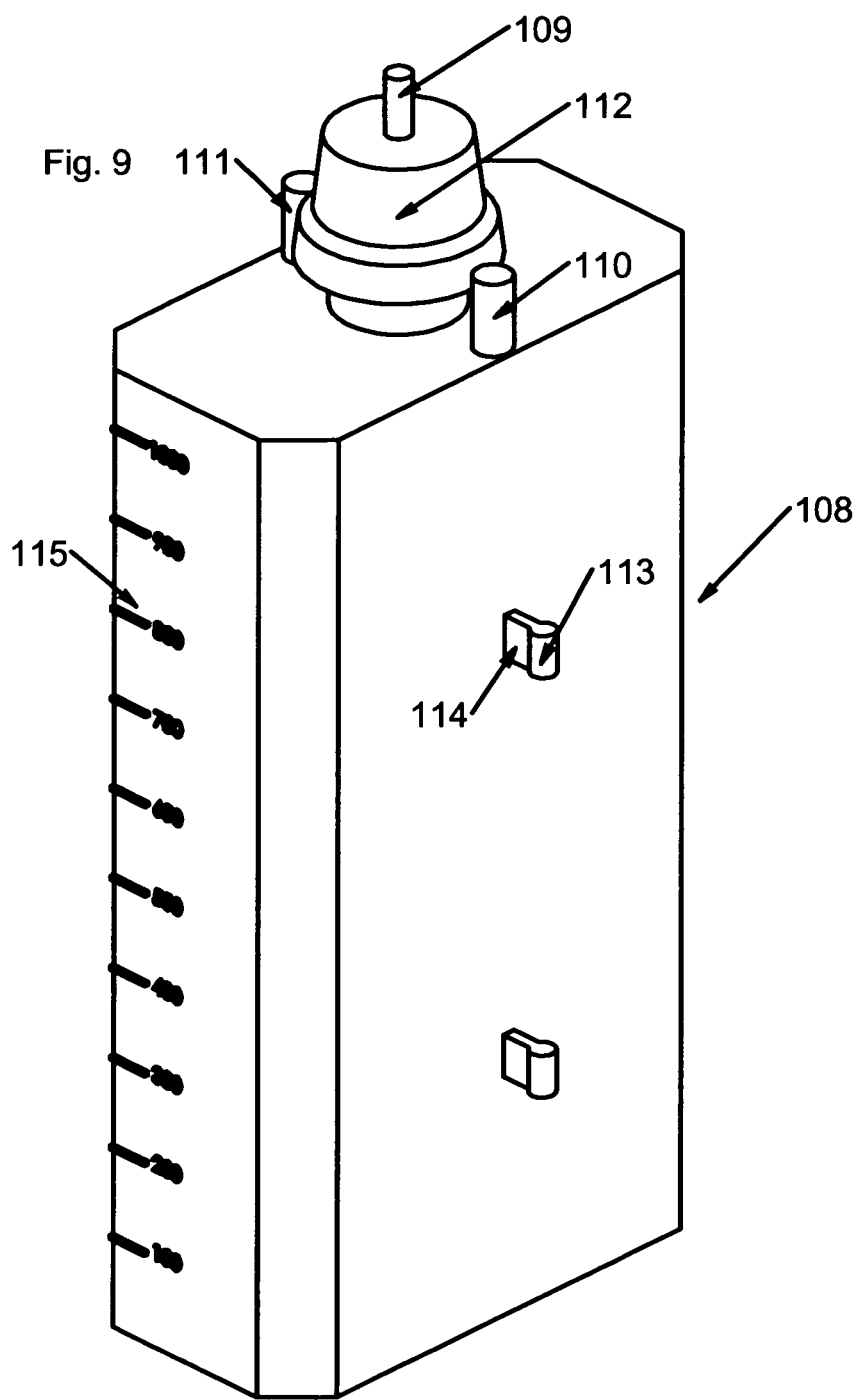

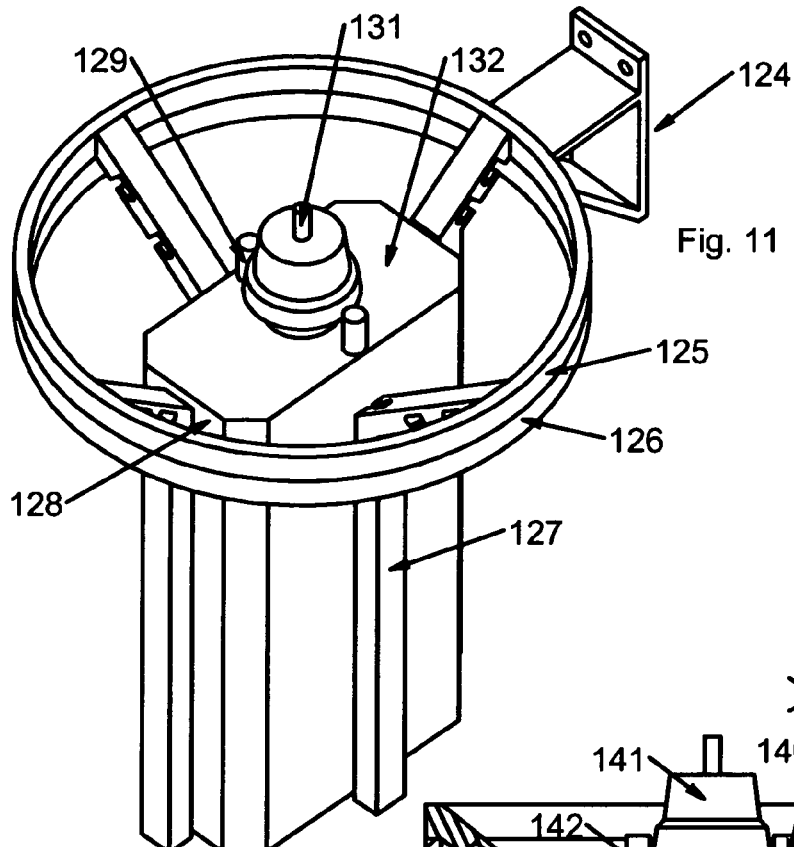
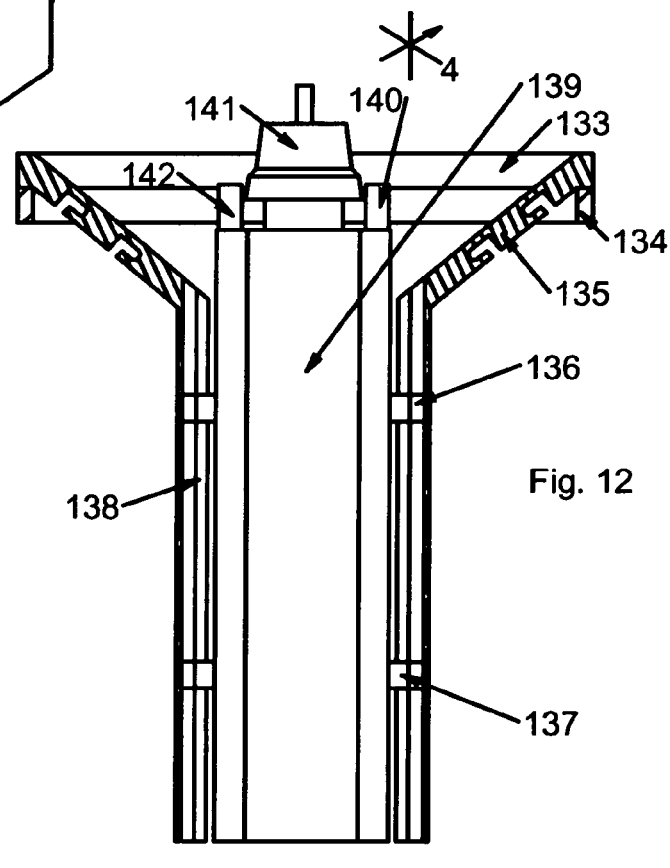
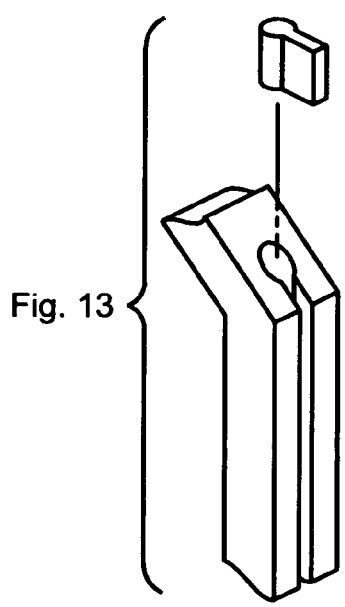

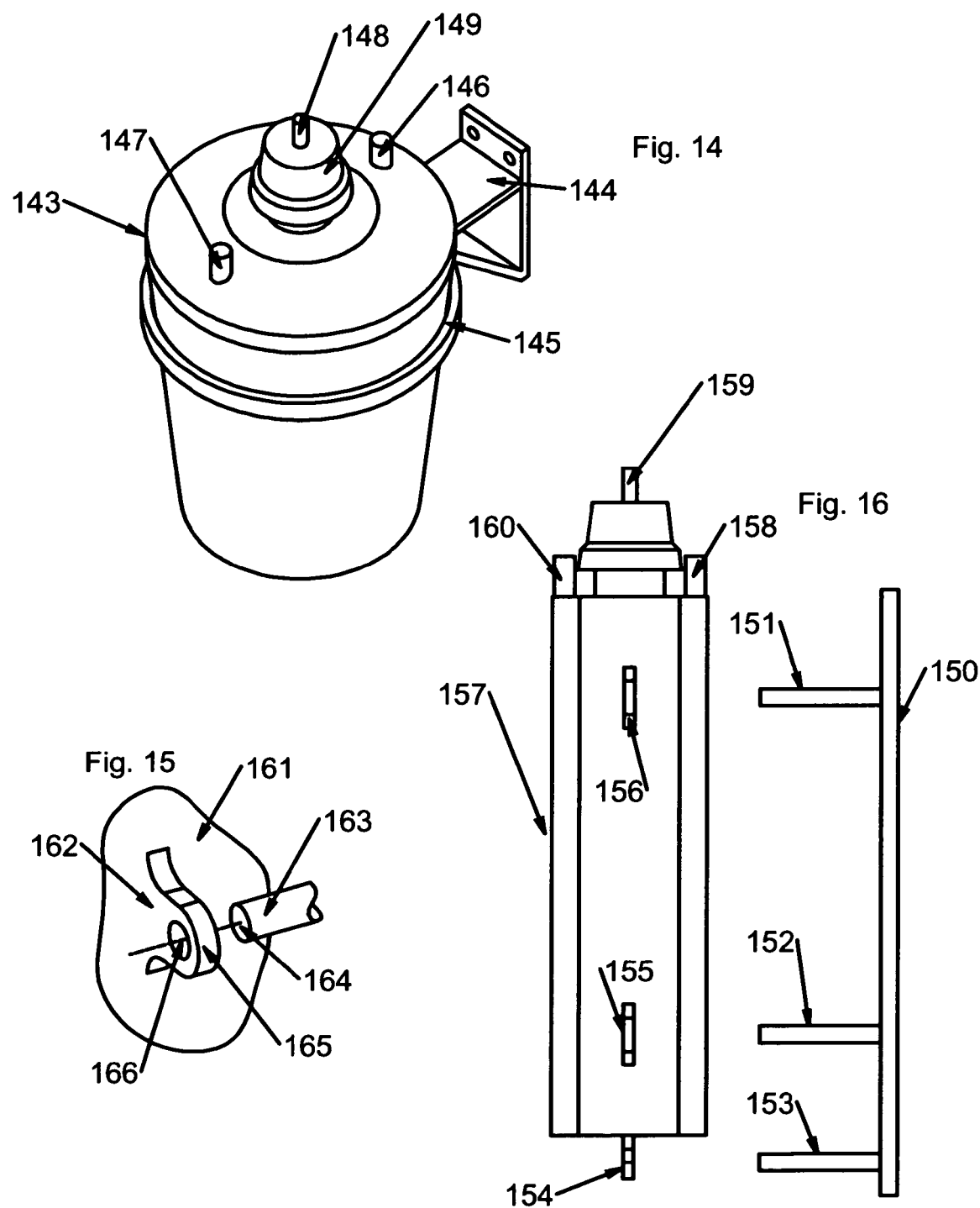

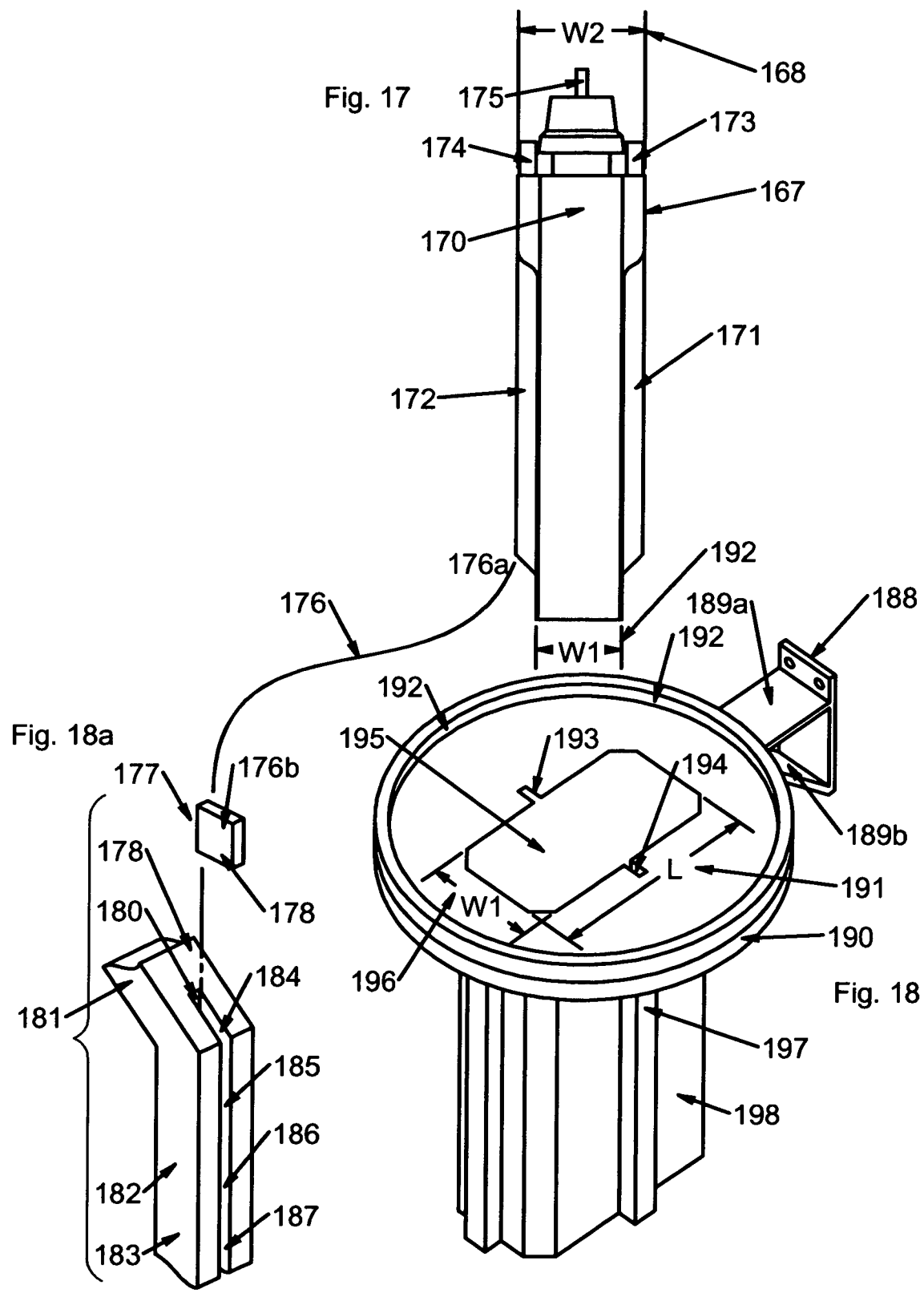

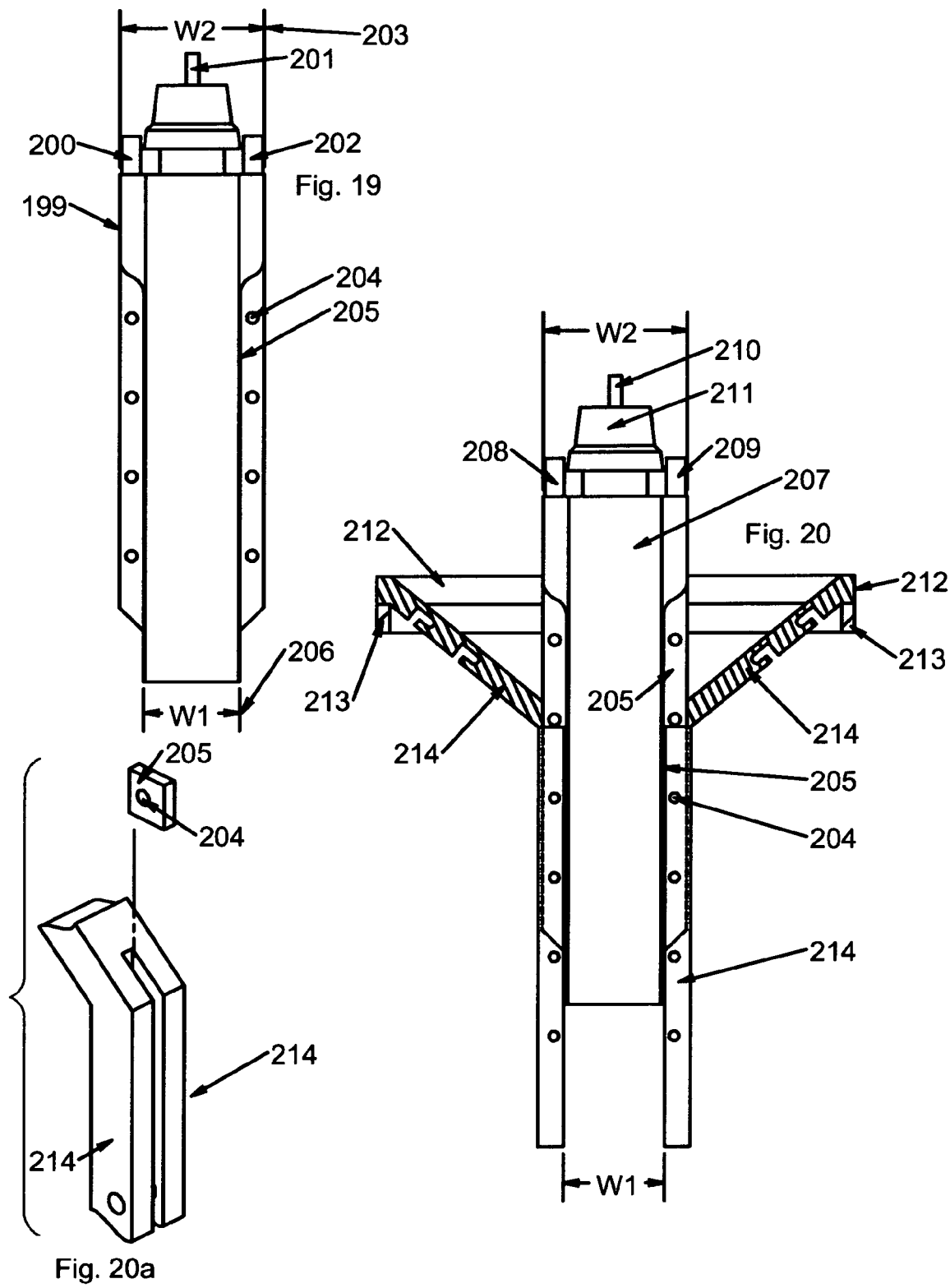

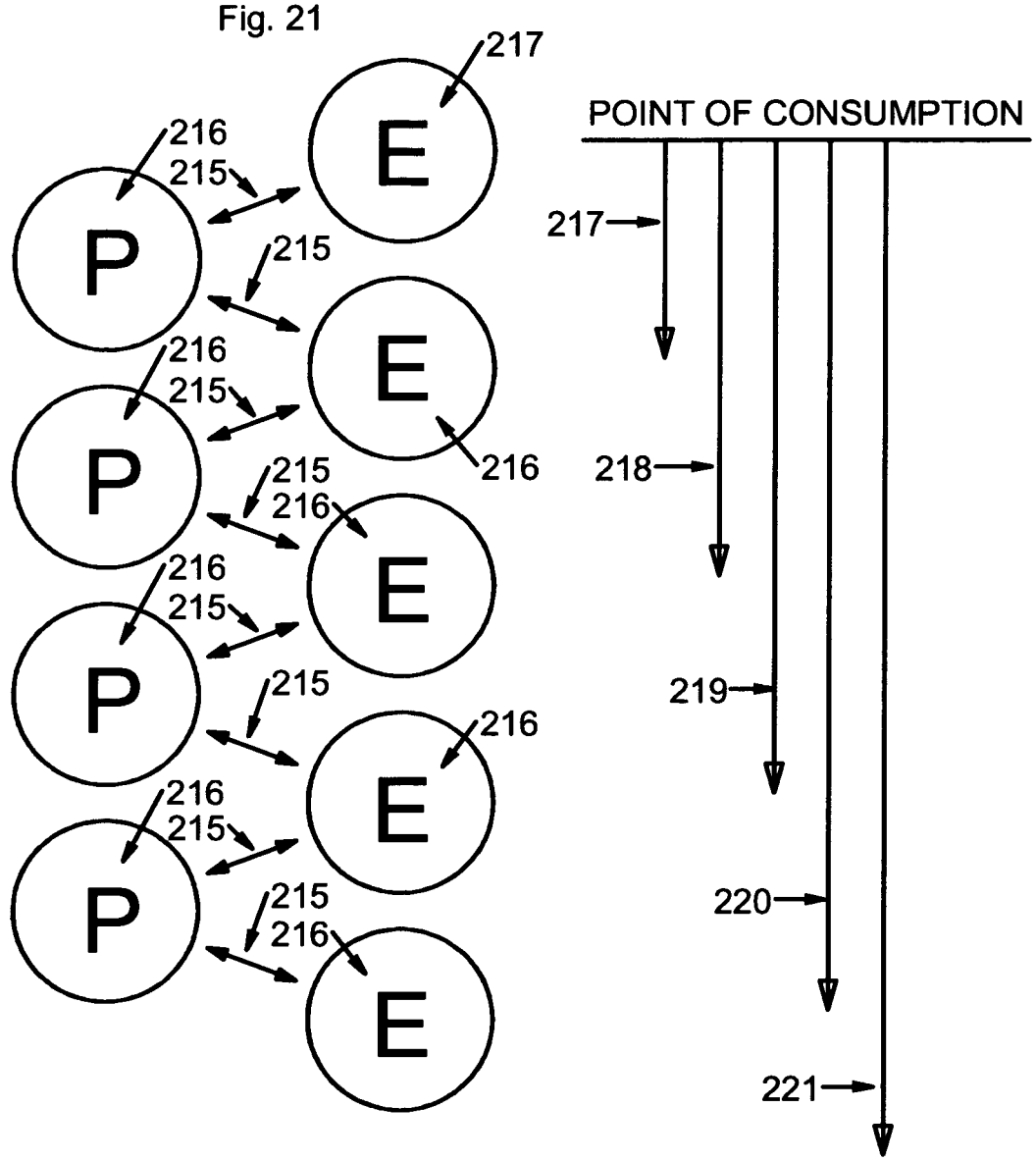

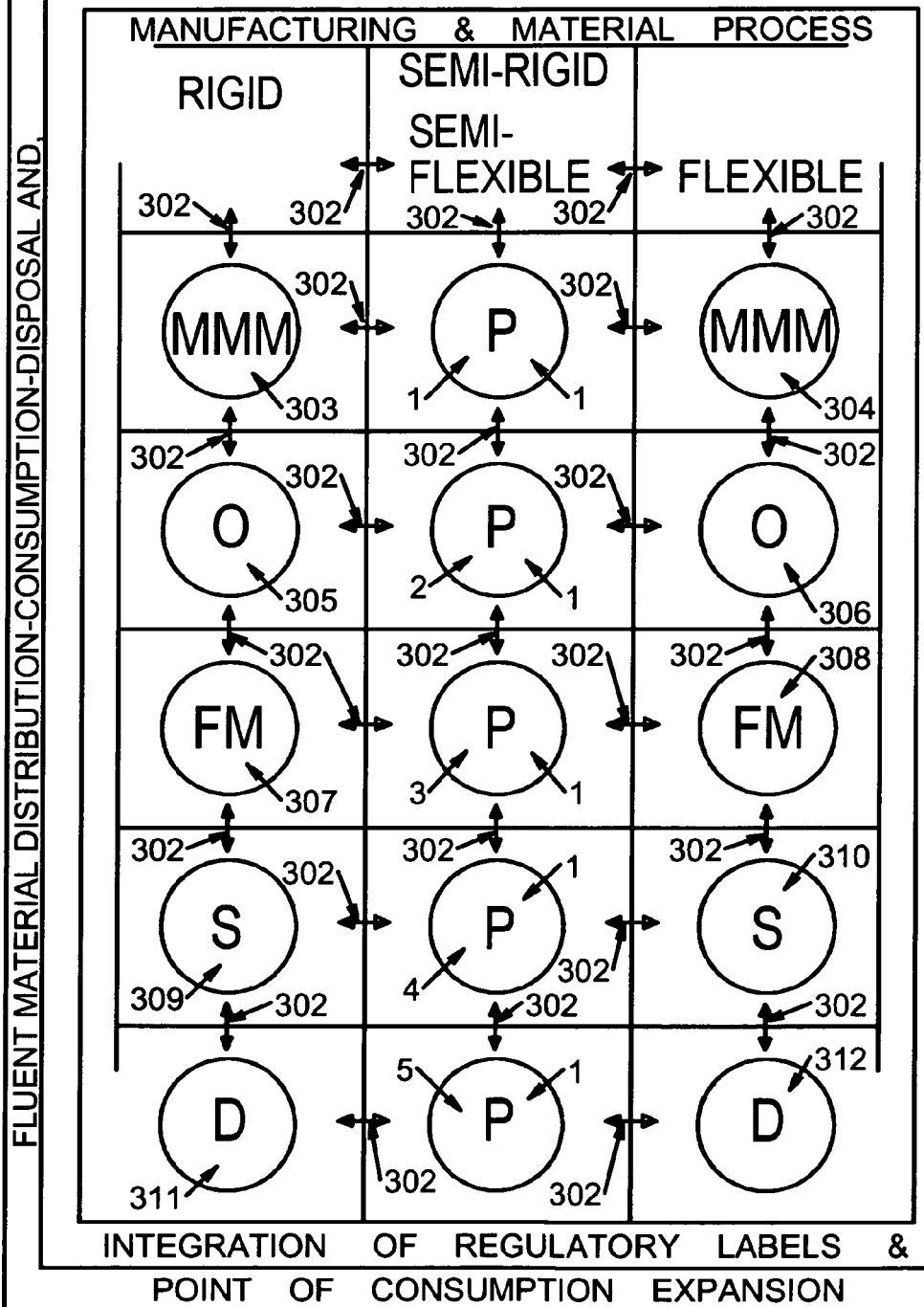

STERILE LIQUID MATERIALS DISTRIBUTION, CONSUMPTION AND MATERIAL WASTE DISPOSAL METHOD AND APPARATUS

CROSS REFERENCE TO RELATED APPLICATIONS

This patent application is a continuation of U.S. patent application Ser. No. 10/280,731 which was filed on Oct. 26, 2002 which claims the benefit under 35 U.S.C. 119(e) of U.S. Provisional Patent Application Ser. No. 60/346,416 which was filed on Nov. 1, 2001.

Subject matter filing history—This patent application is intended to be a continuation of U.S. patent application Ser. No. 10/280,731 filed on Oct. 26, 2002 which claims the benefit of Provisional Patent Application Ser. No. 60/346,416 filed on Nov. 1, 2001. This patent Application consolidates and continues the embodiments, methods and apparatus of U.S. Provisional patent Application Ser. No. 60/346,416 and literally incorporates by reference the subject matter herein directly, by combination and subcombination together with the subject matter of this patent application. This patent application incorporates by reference herein Provisional Patent Application Ser. No. 60/346,416 filed on Nov. 1, 2001.

FIELD OF THE SUBJECT MATTER

This application relates to the field(s) of supply chains and distribution and consumption of sterile/aseptic liquid/fluent materials. This application also relates to the consumption and collection and disposal chain of waste fluent materials. This subject matter also relates to the manufacturing processes and handling systems for fluent materials packaging in the medical field.

SUMMARY OF THE SUBJECT MATTER/EMBODIMENTS

Sterile/Aseptic liquid materials are supplied, consumed and disposed of by a coordinated, manufactured packaging/handling system and structured for connectability as a fluent material disposal packaging/handling system and integrated into/with patient care. The system comprises a supply and disposal chain system and expands "point(s) of consumption (s)" for sterile/aseptic liquid/materials manufacturing and processes. The embodiments of the subject matter disclosed herein comprise interposing passage conduit structures between similar or dissimilar embodiment enclosures of a fluent material handling system. The system also discloses the many applications whereby interposing passage conduit structures between enclosures made from sterile liquid packaging manufacturing processes and other collection and disposal events may have positive impact on the supply and disposal chain associated therewith. The systems enclosure (s) embodiments may be the same enclosure, a different enclosure and the enclosure may function as an origin, source or delivery destination of fluent materials. In this system the patient may function as an origin, source or delivery destination. The passage conduit structures link the delivery of sterile liquid packaging with collection and disposal packaging by interposition there-between, and broaden point of consumption by the interposition there-between and integration with the health care patient. This subject matter also discloses interposing passage conduit structures manufactured and made for the coordinated connectability, coaptibility and interposition between clean/sterile hermetically sealed sterile liquid packaging and other collection like containers and integrates modes of patient care treatment. Supply chain efficiency, and the potential for reducing medical waste, reducing inventory, reducing costs is the innovation of the herein disclosed subject matter/system. The system is a coordinated manufactured system of enclosures and passageway conduit structures, connectable at port structures for the volumetric assessment and/or matching of incoming/distribution of sterile/aseptic liquids with outgoing/disposal materials. The system is intended to address the supply chain. The subject matter/system offers the customer the planning and matching of in and out going fluent materials and the utilization of sterile liquid delivery packaging for collection and disposal of other fluent materials. The system encompasses generally going from clean to dirty, but the subject matter is not limited to that due to reprocessing potential and other circumstances. Points of consumption may be broadened and expansion may be created characterized as going from the supply side to the disposal side by interposing conduit structures there between or, created characterized as going from the disposal side to the supply side by interposing conduit structures there-between, and based on how the system maybe creatively characterized/described. The enclosure/enclosed space of the herein disclosed sterile liquid/aseptic package container embodiments may well be suited for the enclosing/handling of other materials. These enclosures structures, and the passage conduit structures herein disclosed are manufactured with/for conduit structures and coordinated ports structures coordinating the expansion of consumption for coaptability between sterile liquid packaging and broadening consumption to/with other types of packaging and handling of fluent materials. A sterile liquid package of the embodiments disclosed herein have systematized linkability for uses that coordinate the expansion of the points of consumption to supply and disposal and utilized at the creative discretion of the consumer. The goal of the embodiments/innovations disclosed herein are to empower the consumer to have/make creative decisions for supply chain improvements.

Volumetric enclosures provides methods and apparatus for teaching, generating and deriving supply chain efficiency methods and improvement potential. Prime manifold enclosures methods and apparatus provide for deriving and generating efficiency by volumetric displacement and volumetric replacement of dissimilar materials and volumetric displacement and volumetric replacement of material having dissimilar origin. Prime manifold enclosures interposed for cooperative coaptation and flow path communication continuity between gradient matrix flow paths for volumetrically displacing and volumetrically replacing dissimilar materials and volumetrically displacing and volumetrically replacing materials of dissimilar origin. The displacement and replacement of materials may occur from and to a sterile liquid package, hermetically sealed and delivered/distributed with a sterility assurance level required for the delivery of sterile/aseptic liquid packaging to the same package connectable for the disposal of a material not delivered in the package as origin. In process flow continuity embodying volumetric displacement and replacement of distinct/different materials of distinct/different origin interposing manifold/enclosures comprising materials having rigid, and or semi-rigid, and or semi-flexible and or flexible construct characteristics are disclosed for ingressing and egressing fluent materials along gradient pressures flow matrix patterns by the occurrence of differential flow pressures. The embodiment enclosures are interposed along the plow pattern matrices and fluent materials impelled/expelled by pressure gradient inducing events. Flow matrix pressure changes impel/expel fluent materials by any plurality of dynamic causes in the singular or plural sense. Structured cooperation/coaptability and flow matrix composite coaptation interposes passage conduit structures between prime manifold enclosures and interposes prime manifold enclosures between variant causes of pressure gradient change resulting in fluent materials impelling conferring efficiency advantages along the associated supply chains. Passage conduit structures manufactured and made for cooperative coaptation and connectability and interposed between the sterile fluent materials package and the collection package, the clean and the dirty, the incoming and the outgoing. New Methods for deriving fluent flow matrix patterns interposing prime manifold enclosures between flow gradient pressure differentials are taught. New Apparatus for generating new matrix patterns comprising fluent materials manifolds cooperatively structured for creating integrated composite communication flow matrix pathways are disclosed. New Supply chain efficiency advantage potential(s) are conferred in part by expansion of traditional points of consumption across the sterile/aseptic/clean enclosure line to the dirty/collection/disposal line, and across distinct traditional disciplines of manufacturing and care by the interposition of prime manifold enclosures between distinct disciplines previously uncoordinated and the interposition of passage conduit structures manufactured for the coordination and management of fluent material across the sterile/clean and collection/dirty barriers.

For example, in a fluent material handling system, for handling dissimilar fluent materials of dissimilar origin and intended for dissimilar delivery destination said system including a supply chain for barrier enclosures therefore, a method of increasing supply chain efficiency comprises the steps of constructing a prime manifold barrier enclosure with port structures for ingress and egress of dissimilar fluent materials, fitting said port structures with passage conduit structures coapted for connecting said enclosure with fluent materials sources and delivery destinations, and displacing and replacing said dissimilar fluent materials from and to said enclosure and said sources and said enclosure and said delivery destinations, whereby supply chain efficiency is increased by reducing supply costs and quantities of said enclosures. The embodiment of this system wherein said barrier enclosure has a variable cubic/volumetric capacity. The embodiment of the system including the further step of collecting one or more waste fluent materials in said enclosure for disposal thereof. The embodiment of this system including the further step of applying/providing printed and graphic symbols instructions and other indica in text graphics and/or images on the surface or along with said embodiment in teaching creative packaging, conservation re-cycling supply chain efficiency and environmental awareness. The embodiment of this system wherein said displacing and replacing step occurs and or is controlled by application of differential pressure between said barrier enclosure and said sources and said delivery destinations. The embodiment of this system wherein said displacing and replacing step is affected by the force of gravity. The embodiment of this system wherein said barrier enclosure is constructed from rigid material. The embodiment of this system wherein said barrier enclosure is constructed from semi-rigid material. The embodiment of this system wherein said barrier enclosure is constructed from semi-flexible material. The embodiment of this system wherein said barrier enclosure is constructed from flexible material. The embodiment of this system wherein said fluent material handling system is applied to fluent materials in human health care procedures. The embodiment of this system wherein said fluent material handling system is applied to a continuum of care procedures for a health care patient.

In another embodiment example in a fluent material handling system for handling dissimilar fluent materials of dissimilar origin and intended for dissimilar delivery destinations said system including supply and disposal chain for said fluent materials and barrier enclosures therefore, a method of increasing supply and disposal chain efficiency potential comprising the steps of, constructing a prime manifold barrier enclosure with a plurality of ports for ingress and egress of dissimilar fluent materials, fitting said port structures with passage conduits coapted for connecting said enclosure with dissimilar sources and delivery destinations for dissimilar fluent materials, displacing and replacing said dissimilar fluent materials from and to said enclosure and said dissimilar sources and delivery destinations, collecting one or more fluent materials in said enclosure, conditioning said enclosure and said waste fluent material for disposal, whereby supply and disposal chain efficiency potential is increased by reducing supply costs and quantities of said enclosures, quantities and costs of disposal of said enclosures and waste fluent materials and environmental impact therefrom. The method of this embodiment wherein said enclosure has variable cubic/volumetric capacity. The method of this embodiment enclosure wherein said displacing and replacing step is controlled by application of differential pressures between said barrier enclosure and said sources and said delivery destinations. The method of this embodiment wherein said displacing or replacing step is effected by the force of gravity. The method of this embodiment wherein said barrier enclosure is constructed from rigid material. The method of this embodiment wherein said barrier enclosure is constructed from semi-rigid material. The embodiment of this enclosure wherein said enclosure is constructed from semi-flexible material. The method of this embodiment wherein said barrier enclosure is constructed from flexible material. The method of this embodiment wherein said fluent material handling system is applied to fluent materials in human health care procedures. The method of this embodiment wherein said fluent materials handling system is applied to a continuum of care procedures for health care patient(s). The method of this embodiment for creating supply and disposal chain efficiency.

In another embodiment example a method of handling dissimilar materials of dissimilar origin comprising the steps of constructing a prime manifold enclosure with port structures for ingress and egress of dissimilar fluent materials, fitting said port structures with passage conduit structures coapted for connecting said enclosure with fluent material sources, displacing and replacing said dissimilar fluent materials from and to said enclosure and said sources, whereby supply chain efficiency for said enclosures is increased by reducing supply costs and quantities. A method of this embodiment wherein said barrier enclosure has a variable cubic capacity. A method of this embodiment including the further step of collecting one of more waste fluent materials in said enclosure for disposal thereof. The method of this embodiment including the further step of providing and or applying printed and or graphic symbols, instructions and other indica with, on the surface or provided with said enclosure teaching conservation, recycling supply chain efficiency and environmental awareness. The method of this embodiment wherein said displacing and replacing step is controlled and/or occurs by application of differential pressure between said barrier enclosure and said sources and said delivery destinations. The method of this embodiment wherein displacing and replacing step is controlled by application of differential pressure between said barrier enclosure and said sources and said delivery destinations. The method of this embodiment wherein said displacing and replacing step is effected by the force of gravity. The method of this embodiment wherein said barrier enclosure is constructed from rigid material. The method of this embodiment wherein said barrier enclosure is constructed from semi-rigid material. The method of this embodiment wherein said enclosure is constructed from semi-flexible material. The method of this embodiment wherein said enclosure is constructed from flexible material. The method of this embodiment wherein said fluent material handling system is applied to fluent materials in human health care procedures. The method of this embodiment wherein said fluent material handling system is applied to a continuum of care procedures for health care patient(s). The method of this embodiment for creating supply and disposal chain efficiency.

In another embodiment example a method of handling dissimilar fluent material of dissimilar origin intended for dissimilar destinations comprising the steps of constructing a prime manifold barrier enclosure with a plurality of ports for ingress and egress of dissimilar fluent materials, fitting said port structures with passage conduits coapted for connecting said manifold barrier enclosure with dissimilar sources and dissimilar delivery destinations for dissimilar fluent materials, displacing and replacing said dissimilar fluent material from and to said enclosure and said dissimilar sources and delivery destinations, collecting one or more waste fluent materials in said enclosure and conditioning said enclosure and said waste fluent material for disposal, whereby supply and disposal chain efficiency is increased by reducing supply costs and quantities of said enclosures, quantities and costs of disposal of said enclosures and waste fluent materials and environmental impact therefrom. The method of this embodiment wherein said barrier enclosure has a variable cubic/volumetric capacity. The method of this embodiment wherein said displacing and replacing step is controlled/occurs by application of differential pressures between said barrier enclosures and said sources and said delivery destination. The method of this embodiment wherein said displacing and replacing step is effected by the force of gravity. The method of this embodiment wherein said barrier enclosure is constructed from rigid material. The method of this embodiment wherein said barrier enclosure is constructed from semi-rigid material. The method of this embodiment wherein said barrier enclosure is constructed from semi-flexible material. The method of this embodiment wherein said barrier enclosure is constructed from flexible material. The method of this embodiment wherein said fluent material handling system is applied to fluent materials in human health care procedures. The method of this embodiment wherein said fluent material handling system is applied to a continuum of care procedures for a health care patient(s). The method of this embodiment for creating supply and disposal chain efficiency.

Another embodiment example comprising a fluent material handling system for dissimilar fluent material of dissimilar origin and intended for dissimilar delivery destinations comprising, a prime manifold barrier enclosure with port structures for the ingress and egress of said dissimilar fluent materials, passage conduit structures operatively associated with said barrier enclosures and coapted for selectively connecting said barrier enclosure with sources of said dissimilar fluent materials and said delivery destinations, and, means for selectively creating material movement between said sources of fluent material and said barrier enclosure and said delivery destinations. The apparatus of this embodiment wherein said fluent material handling system is applied to fluent materials in human health care procedures. The apparatus of this embodiment wherein said fluent material handling system is applied to a continuum of procedures for a health care patient. The apparatus and methods of this embodiment for creating supply and disposal chain efficiency.

Another embodiment example in a supply chain for dissimilar fluent material and barrier enclosures therefore, said fluent materials having dissimilar origins and being intended for dissimilar destination, a fluent material handling system comprising a prime manifold barrier enclosure with a plurality of ports from ingress and egress of dissimilar fluent materials, passage conduit structures operatively associated with said barrier enclosures and copated for selectively connecting said barrier enclosures with sources of said dissimilar fluent material and said delivery destinations and means for selectively creating material movement between said sources of fluent material and said barrier enclosures and said barrier enclosures and said delivery destinations to selectively displace and replace dissimilar fluent materials there-between, whereby a reduce number of barrier enclosures required to perform a plurality of separate procedures involving dissimilar fluent materials having dissimilar origin to thereby increase supply and disposal chain efficiency of said dissimilar fluent materials and said barrier enclosures. The apparatus of this embodiment wherein said barrier enclosure has a variable cubic/volumetric capacity. The apparatus of this embodiment wherein said displacing and replacing step is controlled by application of differential pressure between said barrier enclosure and said sources and said delivery destination. The apparatus of this embodiment wherein said displacing and replacing step is effected by the force of gravity. The apparatus of this embodiment wherein said barrier enclosure is constructed from rigid material. The apparatus of this embodiment wherein said barrier enclosure is constructed from semi-rigid material. The apparatus of this embodiment wherein said barrier enclosure is constructed from semi-flexible material. The apparatus of this embodiment wherein said barrier enclosure is constructed from semi-flexible material. The apparatus of this embodiment wherein said barrier enclosure is constructed from flexible material. The apparatus of this embodiment wherein said flexible material handling system is applied to fluent materials in human health care procedures. The apparatus of this embodiment wherein said fluent materials handling system is applied to a continuum of care procedures for a health care patient. The apparatus of this embodiment including the further step of applying and providing printed and graphic symbols and instructions and other indica on the surface, unitary therewith, or with said barrier enclosure teaching conservation, recycling, supply chain efficiency and environmental awareness. The method and apparatus of this embodiment for creating supply and disposal chain efficiency.

BRIEF DESCRIPTION OF THE DRAWINGS

FIG. 3 shows a passage conduit structure having both ends formed for association/coupling with embodiment enclosure port structures, source, origin and/or delivery destination. A portion of the passageway conduit is enlarged and has markings, graduated and incrementally placed or formed unitary therewith along the enlarged portion thereof for the purposes of viewing fluent material rise and measuring the rates of such rise. Simply put this is to function as an inline urimeter, and may be used to measure any types of fluent materials desired for monitoring. The fluent material rise measurement may be effected by clamping/occluding the conduit structure at clamp site B or by the interposition of a mechanical device such as a valve or a stopcock which may be opened and closed at choice for the timing and initiation of metering sequences. This conduit structure is intended to be made of clear transparent materials so material rise may easily be visualized. This conduit structure is intended to measure urine output and may be imposed between enclosure 38 and a urinary drainage catheter.

FIG. 4 show a passage conduit structure embodiment having both ends formed for association with port structures and/or a wound drainage catheter, source, origin or delivery destination. A portion of the passage is enlarged in FIG. 4. The enlarged portion has incremental marking or graduated measurements formed unitary therewith or applied thereon for visualization of fluent material rise within the conduit structure. The conduit structure is made from a clear transparent materials so as visualization of fluent material rise is made easily. Fundamentally, this conduit structure enlargement may function as an inline urimeter for the measurement and rate of urinary drainage output but not limited to that. Fluid rise measurement may be initiated by occlusion of the conduit structure at clamp site B or interposition of a stopcock or valve between the port structure of the barrier enclosure and the passage conduit structure.

FIG. 5 shows an embodiment of a passage conduit structure formed at both ends for connection/coaptation to a port structure and a source, origin or delivery destination. One end may be connected to an enclosure barrier the other end may be connected to a urinary drainage catheter. Said passage conduit structure is show with incremental markings and or graduated markings for the visualization of fluid rise and change of fluid flow output.

FIG. 3, FIG. 4, and FIG. 5 show embodiments which may be made of clear transparent material so that visualization of fluids/fluent materials is easy and may be considered useful and functional in the metering of urine drainage flow from the bladder.

FIG. 6 shows a passage conduit structure formed for connectability to a barrier enclosure for receiving fluent materials from a bladder via a urinary drainage catheter.

FIG. 7 show an embodiment of a passage conduit structure having ends formed at one end for connectability to a fluent material barrier enclosure and at the other end for fitting to a wound drain catheter.

FIG. 8 shows and embodiment of a passage conduit structure having ends formed for connectability and fitting to port structures, sources, origins an delivery destinations and to a barrier enclosure end and for fitting/re-fitting to a source, origin or fluent material delivery destination.

FIG. 6a shows the embodiment of a passage conduit structure with one end formed for connectability and fitting to an intravenous solution barrier enclosure at one end, and for fitting to an intravenous access at the other end. The embodiment depicting the addition to the fluent materials of formularies, anesthetic agents, mixing of pharmaceutical preparations and or drugs being added to the fluent materials at some point along the passage conduit structure and or the barrier enclosure.

FIG. 7a show an embodiment of a passage conduit structure having ends formed, at one end for connection to an enclosure barrier and at the other end formed for connection for intravenous access. The embodiment of FIG. 7a depicting the addition to the fluent materials of formularies, anesthetic agents, mixing of pharmaceutical preparations and drugs and the like at some point along the passage conduit structure and or the barrier enclosure.

FIG. 8a shows the embodiment of a passage conduit structure formed at both ends, at one end for connection to barrier enclosure port structures and at the other end for connection to IV access. The embodiment depicting formularies, anesthetic agents, mixing of pharmaceutical preparations and/or mixing drugs added to/with the fluent materials at some point along the passage conduit structure and or at the barrier enclosure.

FIG. 9 shows an embodiment of a barrier enclosure having port structures and anti-motion grips on the side.

FIG. 11 shows an embodiment of the barrier enclosure resting within a holding support means. The enclosure holder fashioned to fit conveniently within a ring support. Both enclosure support and ring are held by a form of bracket or brace.

FIG. 12 shows another view of the barrier enclosure resting within the holder of FIG. 11 and showing the anti-motion structures slidingly associated with the lower portion of the holder.

FIG. 13 shows a blowup detail of the anti-motion structure on the side of the enclosure embodiments of FIG. 9 and FIG. 10 as a key and keyway type of attachable mechanism. Anti-motion structures of the barrier enclosure is shown slidably engaging the lower portion of the holder to support the side walls of the embodiment for supportive purposes.

FIG. 14 shows an embodiment of an barrier enclosure hermetically sealed having port structures and shaped to be supported within a ring holder.

FIG. 15 shows an alternative embodiment of an anti-motion support and pin holder.

FIG. 16 shows an embodiment of the enclosure holder having pins which feed through a plurality of support structures.

FIG. 17 shows a side view of what would be the barrier enclosure embodiments of FIG. 1 and FIG. 2 depicting the anti-motion struts/supports on both sides of the embodiment.

FIG. 18 shows a ring holder and an attachment to the ring holder for accepting the enclosure embodiment slidably engaging the embodiment up to the point on the embodiment where width one becomes width two. FIG. 18 is a blow up view of a portion of the embodiment showing the slidably engagable portion of the anti-motion strut fitting into the portion of the holder.

FIG. 19 shows an alternative embodiment of barrier enclosures of FIG. 1 and FIG. 2 with this embodiment having small holes formed within the anti-motion struts for stability for pinning.

FIG. 20 shows the embodiment of FIG. 19 being held within an alternative embodiment holder whereby the wholes for pinning line up for holes in the holder for stability.

FIG. 20a shows a blow up of the pinning (pin and hole) assembly whereby the holes of the anti-motion strut may be aligned with the holes of the holder for pinning there through for stability if necessary.

FIG. 21 shows a schematic view and a line chart of how the sterile liquid delivery embodiments of this disclosure are intended to expand the points of consumption along a continuum of care to cross into the uses not requiring sterile liquid packaging. The arrows 215, depict the passage conduit structures interposed between coordinated manufactured coaptation between the enclosure(s) and the patient along a continuum of care. The enclosure embodiment may be similar/dissimilar, and expands the point of consumption as the passage conduit structure interposes the similar/dissimilar barrier enclosure between itself as a sterile liquid package and a non-sterile liquid package and the like.

FIG. 21 shows passage conduits of this embodiment system interposed between the sterile and the non-sterile, interposed between the clean and the dirty, interposed between the sterile liquid package and the package not manufactured for sterile liquid package (which may be the same/similar or different/dissimilar package/barrier enclosure. FIG. 22 sows three schematics A, B & C. In schematic A the circles represent the enclosure as an origin, the enclosure and a delivery destination, the enclosure as a source. It is also intended to show the patient as a potential origin, source and/or delivery destination. The arrows of schematic a are intended to depict passage conduit structures coordinated and manufactured for coaptability and connectability and interposed between origins, sources, delivery destinations and patients or any combination thereof. Example B is intended to show the enclosure as a delivery destination, and/or the enclosure as a source and/or the enclosure as an origin. Example B also intends to show the patient as a source, and/or as an origin and or as a delivery destination. The arrows of example B intend to depict passage conduit structures manufacture for coaptable connectability and interposed the enclosures and the patients as depicted by the schematic. Example C is intended to show the enclosures as a source, the enclosure as an origin, and the enclosure and the enclosure as a delivery destination. Example C also intends to show the patient as a destination, and/or as and origin, and/or as a source. The arrows of example C are intended to depict manufactured connectable and coaptable and connectable passage conduit structures made for interposition between the enclosures and the patient as depicted in example C.

FIG. 25 shows a schematic having to do with enclosure(s) and passage conduit structure reprocessing. It is intended to show that reprocessing may add flexibility and re-application along continuums of care and to further expand the points of consumption of the same/similar barrier enclosures and/or passage conduit structures. The reprocessing may be appropriate for certain circumstances as deemed necessary by the consumer. The straight lines of this schematic show passage conduit structures as manufactured, coapted links interposed between the origins, sources, delivery destinations, and patients interposing similar/same barrier enclosure(s) interposed between distribution of sterile liquid packages and disposal/collection of fluent materials not otherwise distributed as a sterile liquid package, under a variety of circumstances and for a plurality of dynamic events, but not limited to that.

FIG. 26 is a schematic made to show the flexibility and co-integration of how the embodiment(s) enclosure(s) system may be applied to the distribution consumption and disposal of barrier enclosures and passage conduit structures. This diagram is intended to teach open flexibility and application of the herein disclosed embodiment systems and the flexibility potential the consumer may utilize in its consumption, and creation of the maximum supply chain savings benefit. MMM means methods of manufacturing and materials. O means origin(s). FM means fluent material(s). S means source(s). D means destination(s). P means patient(s).

Schematic FIGS. 21 through 26 show by arrows and line linkages how a barrier enclosure embodiment(s) distributed and consumed in sterile liquid package condition, meeting the regulatory and Sterility assurance requirements of the sterile liquid package industry, may be consumed and conditioned for enclosing fluent materials in the collection and disposal of fluent materials. Embodiments are show for this purpose and applied to the subject matter and the embodiments of the entire application in FIGS. 1 through 26 disclosed herein, as well as the aforementioned provisional patent application and the aforementioned non-provisional patent application cited in the first paragraph of this provisional patent application.

DESCRIPTION OF THE DETAILED DRAWINGS

Figure 1:
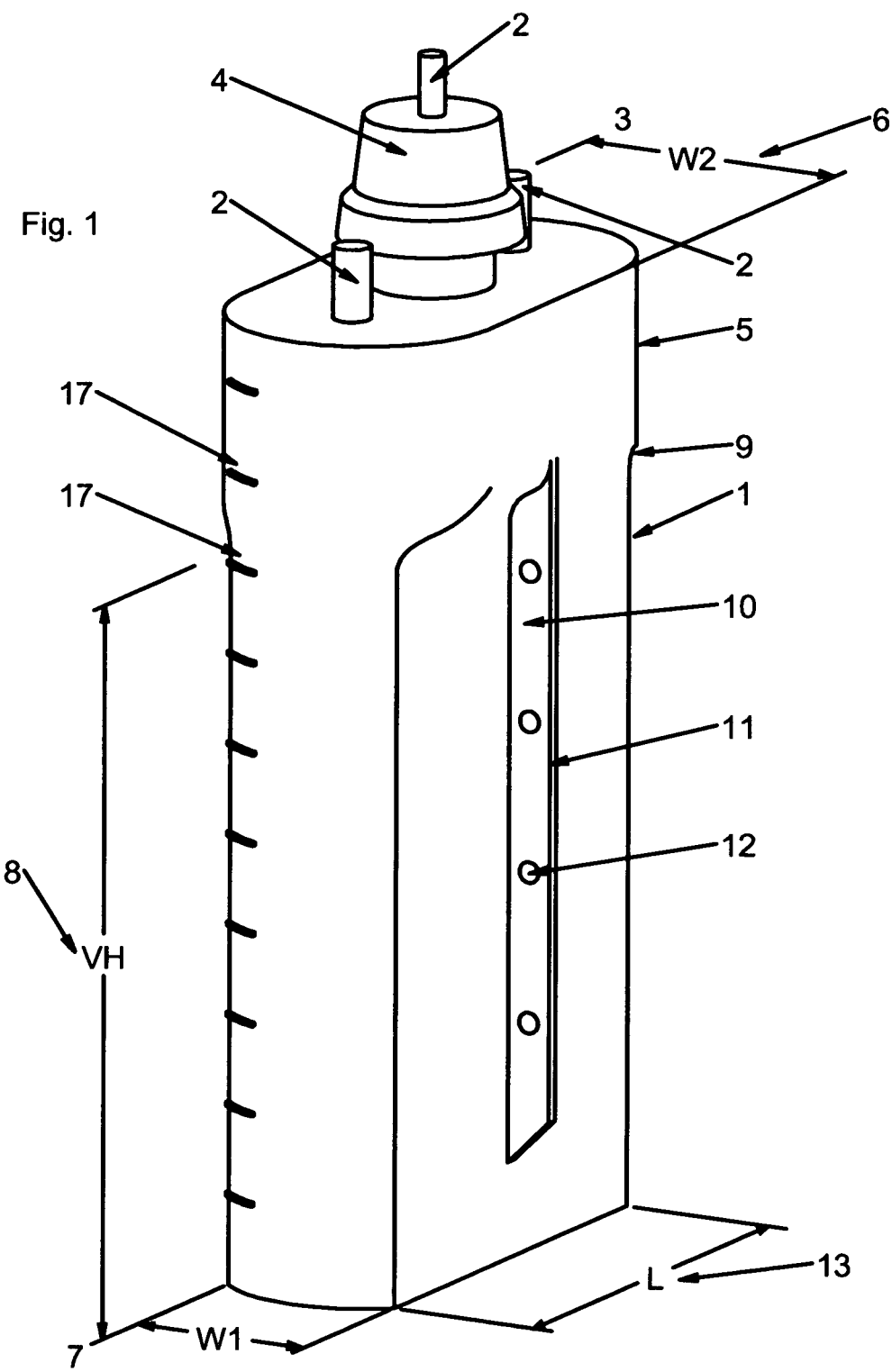
FIG. 1 shows an embodiment enclosure having port structures, anti-motion strut supports and two different widths. The embodiment may be hermetically sealed as with a sterile liquid package or sealed otherwise for handling fluent materials.

In FIG. 1, embodiment 1 has three port structures 2. One port structure is attached to cap closure 4. Embodiment 1 has width 2-6 and width 1-7 and length 13. Variable height portion 8, allows for the enclosure barrier to have different heights/volumes and still fit within the holder of FIG. 18. Embodiment 1 has incremental marking 17 so that fluent material flow rate may be monitored. Embodiment enclosure 1 also has anti-motion strut 10 of sufficient width 11 to maintain anti-motion support. Anti-motions strut 10 has pin hole 12. Embodiment enclosure 1 has two width's whereby width 1-7 changes to width 2-6 at 9 producing a differential dimension ledge at 9. This ledge forms a support 9 and contact point around the edge periphery making a contact point about the embodiment to be held in the aperture of the support holder of FIG. 18.

Figure 2:
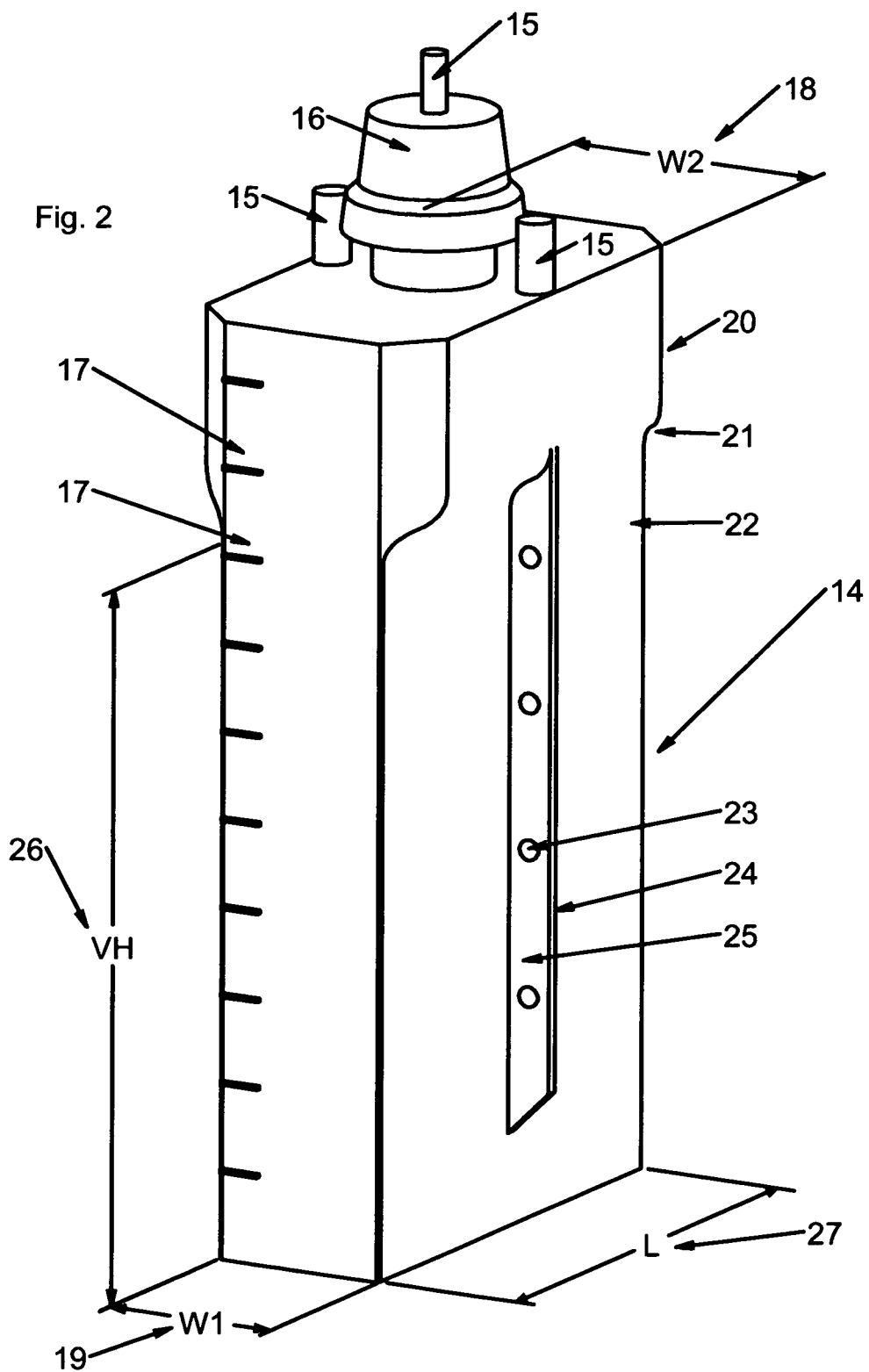
FIG. 2 shows and embodiment having port structures with the port structures lined perpendicular to the port structures of FIG. 1 embodiment. This embodiment barrier enclosure comprises two widths segments and anti motion struts. This embodiment may be hermetically sealed for sterile liquid packaging or sealed otherwise for handling fluent materials.

FIG. 2 comprises enclosure embodiment 14 having three port structures each 15 one port structure 15 is attached to cap 16. Embodiment enclosure 14 has two widths 19 & 18, width 2-18 and width 1-19 and has length 27. Width 1-19 meets width 2-18 at 21, creating differential dimensions at 21, the differential dimensions on each side of the embodiment enclosure forming the ledge(s) for support of embodiment 14 for fitting and being held by the support holder of FIG. 18. Embodiment 14 has variable height 26 for different manufacturable volumes of the embodiments having different overall heights and still fit within the holder support of FIG. 18. Embodiment 14 has incremental markings 17 so that the rate of fluent material flow may be visualized. Anti-motion struts supports 25 having sufficient width 24, and pin hole 23, and similar to anti-motion strut 10 of FIG. 1 may be unitary to the enclosure or may be attached. Pin hole 23 of anti-motion strut/support 25 allow pinning and further securing to the lower holder structure of FIG. 20.

The embodiment of FIG. 3 comprises passage conduit structure having an enlarged portion 31 with incremental marking 32 for the visualization of fluent flow rate changes. Enlarged conduit portion 31, having length 30 and incremental marking 32 is also make of transparent clear materials. Structure 28 may be associated with a urinary drainage catheter or the like and structure 34 may be associated with the enclosure 38. Passage conduit structure 33 may be fitted to a stopcock of valve at A, to stop flow near the enclosure barrier connection site so that fluent material drainage flow may rise in the enlarged portion 31 to monitor drainage output such as would be the case in using a urimeter, but in this embodiment the enlarged portion 31 functions as an in line urimeter. Junction A may comprise a stopcock or a valve or any other similar means of occluding passage of fluent materials during the period for which metering is desired. Similarly, simply clamping passage conduit structure at B may effect the same occlusion during the period for which occlusion is required. The enclosure barrier embodiment of FIG. 3 has port structure 36 manufactured for coaptibility and connectability to the passage conduit structure of FIG. 3.

FIG. 4 shows another embodiment of a passage conduit structure 43, having enlarged portion 41 and enlarged height portion 42. The enlarged portion has incremental marking for visualization and metering the rise of fluent material flow rates. The passage conduit structure of FIG. 4 may be associated with a urinary drainage catheter at 39, or a wound catheter at 39 and connected to an enclosure barrier at 45. FIG. 4 is show to have the same stopcock, valve, or other flow occlusion means as depicted at B.

FIG. 5 comprises an embodiment of passage conduit structure 55, a portion of which said structure has incremental markings 56 along length portion 54 of said conduit structure and intended to function as an inline fluent flow meter (in line urimeter but not limited to that) for measuring/metering the fluent material rise rate for determining the volume/rate of fluent material flow. Passage conduit structure 55 may be clamped at B to occlude fluent flow effecting the flow rise along conduit length 54 and incremental markings 56 may used to determine the flow rate as desired and functioning as an inline fluent material flow meter (inline urimeter but not limited to that).

FIG. 3 FIG. 4, and FIG. 5 show passage conduit structures having transparency and being made of materials clear enough for visualization of fluent materials rise along lengths 30, 42, and 54 of the passage conduit structures shown.

FIG. 6, FIG. 7, and FIG. 8 respectively each show enclosure barriers 69, 69a and 83, manufactured with port structures for coaptive connectability to passage conduit structures 65, 71, & 77. The passage conduit structures having ends 66, 72 & 78 manufactured for coaptive connectability to port structures of enclosures 69, 69a and 83 at one end and intended for receiving materials from coaptive connectability to a urinary bladder drainage catheter, a wound drainage catheter or from a source-origin-delivery-destination or a health care patient as shown in FIGS. 21 through 26.

FIGS. 6a, 7a & 8a show embodiment enclosures 84, 100 & 101 each having port structures 87, 94 and 103 and manufactured for coaptive connectability to passage conduit structures 88, 96 and 104. Enclosures 84, 100 & 101 are manufactured for coaptive connectability to origins sources and delivery destinations and patients as shown in the schematics of FIGS. 21 through 26 and are intended to for coactive connectability to intravenous access through end structures 90, 98 & 106. Formularies, anesthesia agents, pharmaceutical preparations, mixing of drugs and preparations and administering and dosing treatments may take place along passage conduit structures 89a & b, 97a & b and 105a & b or may take place at the sites of enclosures embodiment structures 84, 100 and 101.

In an embodiment, a first conduit egresses material from a container towards a natural anatomic site of a health care subject, a second conduit transfers material towards and/or into said container from different natural anatomic sites of a health care subject and a third conduit egresses vacuum flow out of said container towards a source of vacuum.

The embodiment of FIG. 9 shows enclosure 108 having port structures 110, 111 and 109 and cap 112. Mounted one the side of embodiment enclosure 108 shows anti-motion grip 113 having two dimensions 114 and 113. Enclosure 108 shows incremental marking 115.

Figure 10:
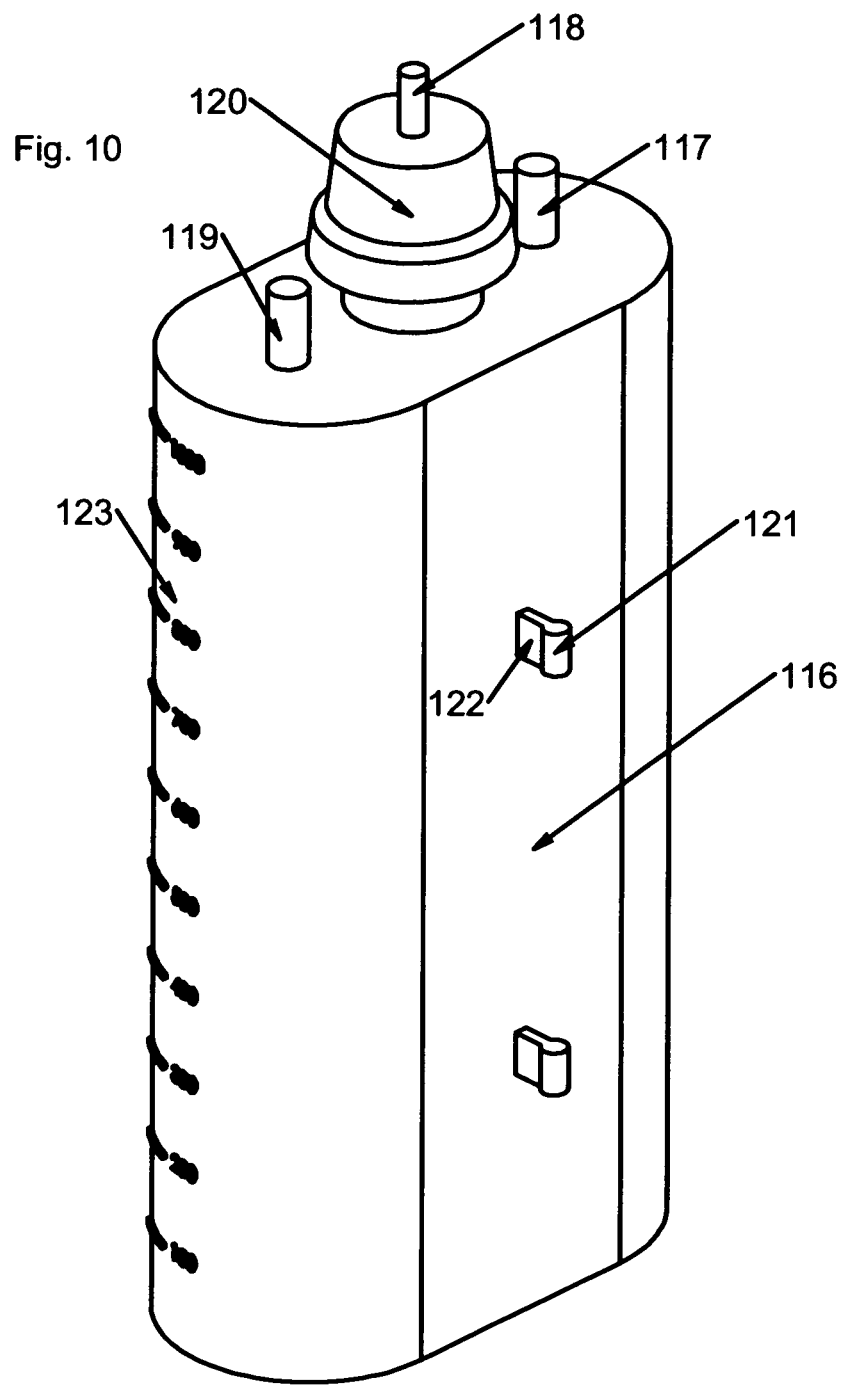
FIG. 10 shows another embodiment barrier enclosure having port structures and anti-motion grip structures on the side.

The embodiment of FIG. 10 comprises an alternative barrier enclosure 116 having overall differing shape (rounded edges) having port structures 117, 118 and 119 and cap 120. Incremental markings 123 are shown. Anti-motion grips 121 and 122 having two dimensions 121 & 122 are associated therewith.

FIG. 11 shows embodiment of enclosure holder 125 which is fashioned to be held by resting/holding ring 126. Ring support 125a 125b and 125c are structurally attached to ring 125. Barrier enclosure 132 slidable engages the vertical enclosure supports of 125a 125b and 125c.

FIG. 12 shows barrier enclosure 139 in resting position within ring holder 125. Enclosure 139 has ports structures 142, 141 and 140 positioned and accessible for access to passage conduit structures. Vertical support 138, 136 and 137 slidably engage anti-motion grips as shown in FIGS. 9 and 113 and 114 and as shown in FIG. 10 as 121 and 122. The slidably engagable grip system fit is shown more visibly in blow up FIG. 13 whereby anti-motion grip 114m 113 and 121 and 122 are placed in slidable engagement with vertical support 136 forming a key and key hole/keyway sliding relationship.

FIG. 14 shows ring holder 145 supported by mount 144. Barrier enclosure 143 has port structures 147 148 and 146 and cap 149.

FIG. 16 shows an alternative embodiment of anti-motion struts. Barrier enclosure 157 has port structures 158 and 159 & 160 and has anti-motion supports 156 and 155 and 154. Stability pin 151, 152, and 153 are mounted to support 150 and are located and position to accept the holes associated with enclosure 157 and racked/placed on holder 150 as the pins are placed through the holes as depicted in FIG. 15.

FIG. 15 is a close up of anti-motion support 162 having hole 166 and may be made unitary or associated with enclosure housing wall 161. The close up of FIG. 15 shows the pin and hole relationship of pins 151, 152, 153 and how they would be used in pinning holes 156, 155, and 154 as positioned around enclosure 157 for anti-motion support means. This engagement creates a plurality of anti-motion support for enclosure 157.

FIG. 17 shows embodiment 170 having width 1-169 and width 2-168. Anti motion support 172 and 171 are intended to fit within holder slot 193 & 194 of FIG. 18. Enclosure 167 has port structures 174, 175 & 173. Width 1-169 of embodiment 167 of FIG. 17 is intended to correspond width 1 of embodiments enclosures 1 of FIG. 1 and embodiment enclosure 14 of FIG. 2, and width one-196 of in FIG. 18 but width one-196 of FIG. 18 is slightly larger for easy accommodation of the aforementioned enclosure embodiment. Length L 191 of FIG. 18 corresponds of length L 27 of FIG. 2 and length L13 of FIG. 1 however length l 191 of FIG. 18 is slightly larger for easy accommodation of the aforementioned enclosure embodiments. Width 1-169 and length (not shown but inferred by lengths 27 and 13 *f* FIGS. 1 & 2) of FIG. 17 is intended to slide into aperture 195 in surface/space of 191 of holder 192. Ridged surface 172*a* and 172*a* of FIG. 17 is intended to rest on surface 191 supporting enclosure 167 in holder 192. Holder 192 is intended to conveniently fit onto a ring 190. Ring 190 is supported by braces 189*b* and 189*a* and mounted to support 188. FIG. 18*a* shows lower support 182. Lower support 182 has slot 180 and shows slidable engagement of anti-motion support 176*a*.

FIG. 19 shows embodiment enclosure 199 having anti-motion supports 205 which has pinning holes 204. Enclosure 199 also has width 1-206 and width 2-203. Embodiment enclosure 199 slidably fits into holder 212. Holder 212 conveniently fits onto ring 213. Lower support 214 is slotted as shown in blow up FIG. 20*a*. Lower motion support 205 has pin hole 214*a* which may be conveniently aligned with anti-motion support pin hole 204 and pin for anti-motion stability. FIGS. 17, 18, 18*a*, and FIGS. 19, 20 and 20*a* are intended to show alternative enclosure holding methods and apparatus for enclosure embodiments of FIG. 1 and FIG. 2. The change in width from width 1(7, 19, 169, 206) to width 2(6, 18, FIG. 17-168, FIG. 19-203, FIG. 20 W2) creating a ridge or resting ledge for contact support to contact surface/stop 191 whereby enclosure portion 199 of FIG. 19 may rest above the surface of aperture support 191 of FIG. 18.

FIGS. 21 through 26 show the interrelationship and integration of the distribution and delivery utilization sterile liquid/aseptic packaging manufacturing processes with/to the collection and disposal of fluent materials as described and disclosed in this application. The embodiments, apparatus and methods herein disclosed are intended for creative integration and utilization for the maximum desired/created application for supply chain efficiency potential.

What is claimed is:

1. A supply chain and disposal chain method comprising,
   a) egressing a fluid from a container, said fluid enclosed in said container during transfer from manufacturing to a point of consumption, said consumption to include said fluid being egressed away from a health care subject towards non-anatomic locations,
   b) relocating said container after said egress and away from said non-anatomic locations said relocation to include transfer of waste material toward and/or into said container from sources of natural anatomic locations of a health care subject, whereby a vacuum flow is established, said vacuum flow configured to extend between a source of said vacuum flow and said natural anatomic locations, a first conduit connected to said container and configured to direct said flow away from said container toward said source of vacuum flow, a second conduit connected to said container and configured to direct said vacuum flow and said waste material toward and/or into said container, a vacuum draw path is established by said first conduit, said second conduit and said container.

2. A supply chain and disposal chain apparatus of claim 1 wherein said fluid comprises an intravenous solution.

3. A supply chain and disposal chain apparatus of claim 1 wherein said fluid comprises an irrigating solution.

4. A supply chain and disposal chain apparatus of claim 1 wherein said fluid comprises a sterile liquid.

5. A supply chain and disposal chain apparatus of claim 1 wherein said egress includes combination of said fluid and an anesthetic.

6. A Supply chain and disposal chain apparatus of claim 1 wherein said egress includes combination of said fluid and a medicament.

7. A supply chain and disposal chain apparatus of claim 1 wherein said fluid comprises an aseptic material.

8. A supply chain and disposal chain method comprising,
   a) egressing fluid from a container toward anatomic locations of a health care subject,
   b) relocating said container after said egress and away from said anatomic locations said relocation to include transfer of waste material drawn by a vacuum source toward and/or into said container from different natural anatomic locations of a health care subject, whereby a vacuum draw path is established, said vacuum draw path configured to draw vacuum flow out of and away from said container along a first conduit towards said vacuum source, said vacuum source configured to draw said vacuum flow along a second conduit towards and/or into said container, said vacuum source configured to draw said waste toward and/or into said container between said vacuum source and said different natural anatomic locations.

9. A supply chain and disposal chain apparatus of claim 8 wherein said fluid meets a sterility assurance level.

10. A supply chain and disposal chain apparatus of claim 8 wherein said fluid comprises an irrigating solution.

11. A supply chain and disposal chain apparatus of claim 8 wherein said fluid comprises a sterile liquid.

12. A supply chain and disposal chain apparatus of claim 8 wherein said egress includes combination of said fluid and an anesthetic.

13. A supply chain and disposal chain apparatus of claim 8 wherein said egress includes combination of said fluid and a medicament.

14. A supply chain and disposal chain apparatus of claim 8 wherein said fluid comprises an aseptic material.

15. A supply chain and disposal chain method comprising,
   a) egressing a material from a container along a first conduit towards a natural anatomic site of a health care subject,
   relocating said container away from said first conduit and said natural anatomic site after said egress, said relocation to include transfer of waste material towards and/or into said container along a second conduit from different natural anatomic sites of a health care subject, whereby said waste transfer is interposed between a vacuum source and said different natural anatomic sites of a health care subject, said a vacuum source configured to draw vacuum flow out of and away from said container along a third conduit interposed between said container and said vacuum source, said vacuum source configured to cause said waste material transfer along said second conduit.

16. A supply chain and disposal chain apparatus of claim 15 wherein said material comprises an intravenous solution.

17. A supply chain and disposal chain apparatus of claim 15 wherein said material comprises an irrigating solution.

18. A supply chain and disposal chain apparatus of claim 15 wherein said material comprises a medical fluid.

19. A supply chain and disposal chain apparatus of claim 15 wherein said egress includes combination of said material and an anesthetic.

20. A supply chain and disposal chain apparatus of claim 15 wherein said egress includes combination of said material and a medicament.

* * * * *

UNITED STATES PATENT AND TRADEMARK OFFICE
CERTIFICATE OF CORRECTION

Figure 22:
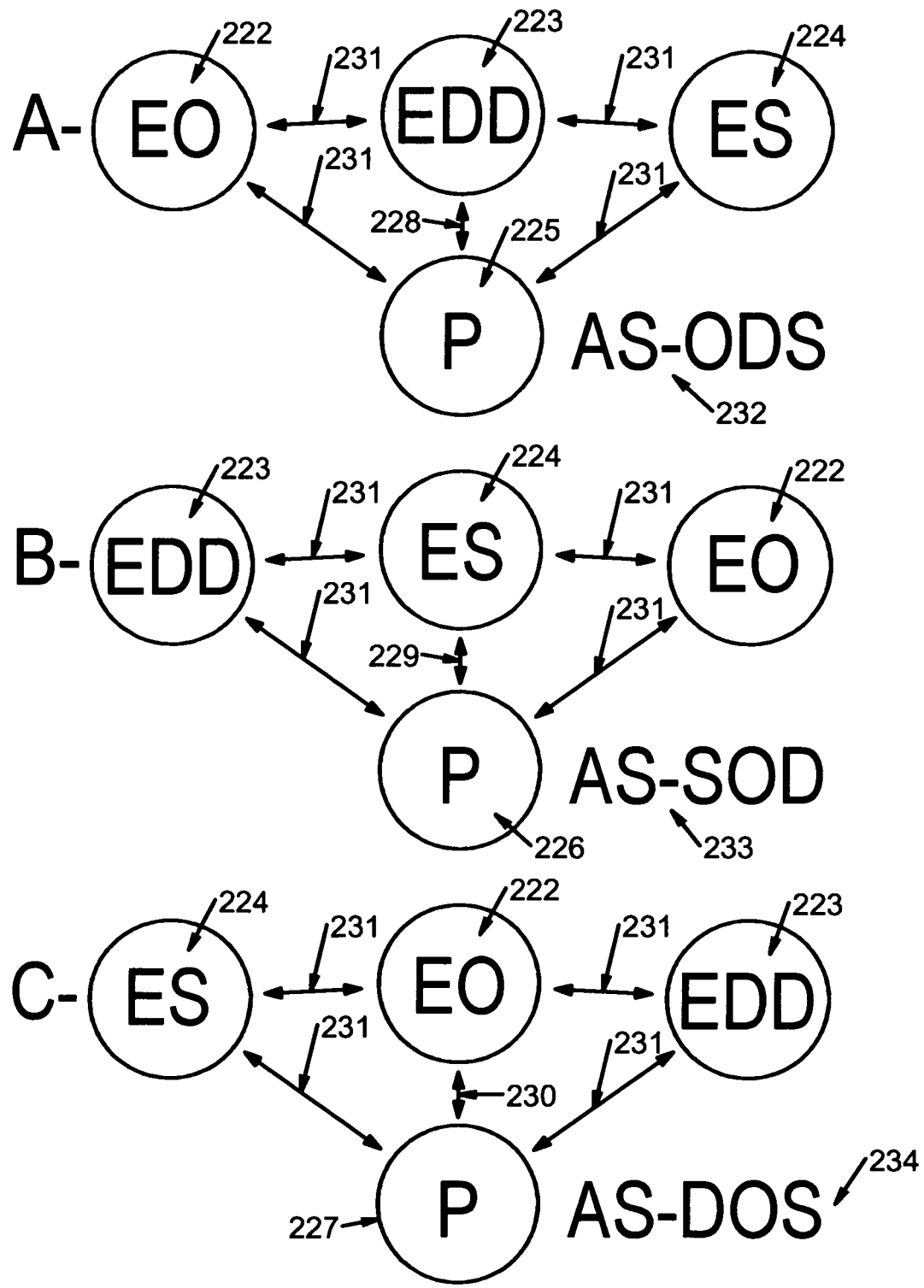
FIG. 22 shows arrows of consumption/uses and arrows with the acronyms having the following meaning. EO means enclosure embodiment(s) as an origin(s). EDD means enclosure embodiment(s) as delivery destination(s). ES means enclosure embodiment(s) as a source(s). P means a patient (body) as an origin(s), as a source(s) and or as a delivery destination(s) but not intended to be in any particular order, but in the order(s) best determined by the customer.
Figure 23:
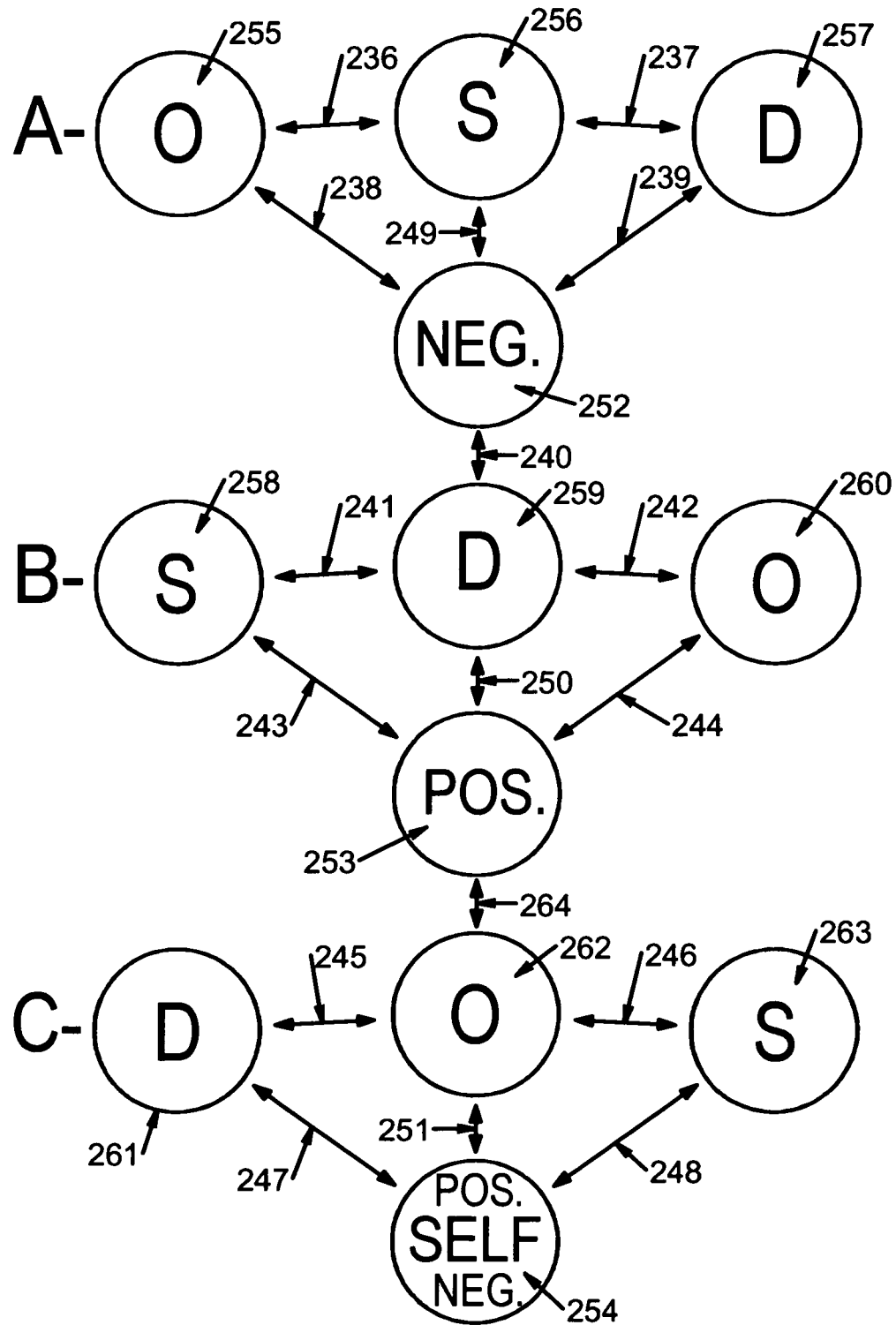
FIG. 23 shows the system differential pressure dynamics of examples A, B & C of FIG. 22 and relates these examples of barrier enclosure consumption with positive, negative and self imposed differential pressures. The self imposed differential pressures may be initiated by wall spring memory or may be initiated by electrical/mechanical means within the enclosure-IE not from a remote source. The arrows of examples A, B & C of FIG. 23 depict passage conduit structures interposed between enclosure embodiments that may function as origins, sources, and/or delivery destinations whereby the same/similar enclosure made sold and used for consumption and manufactured for coordinated connection as a sterile liquid package includes consumption as another type of enclosure barrier.
Figure 24:
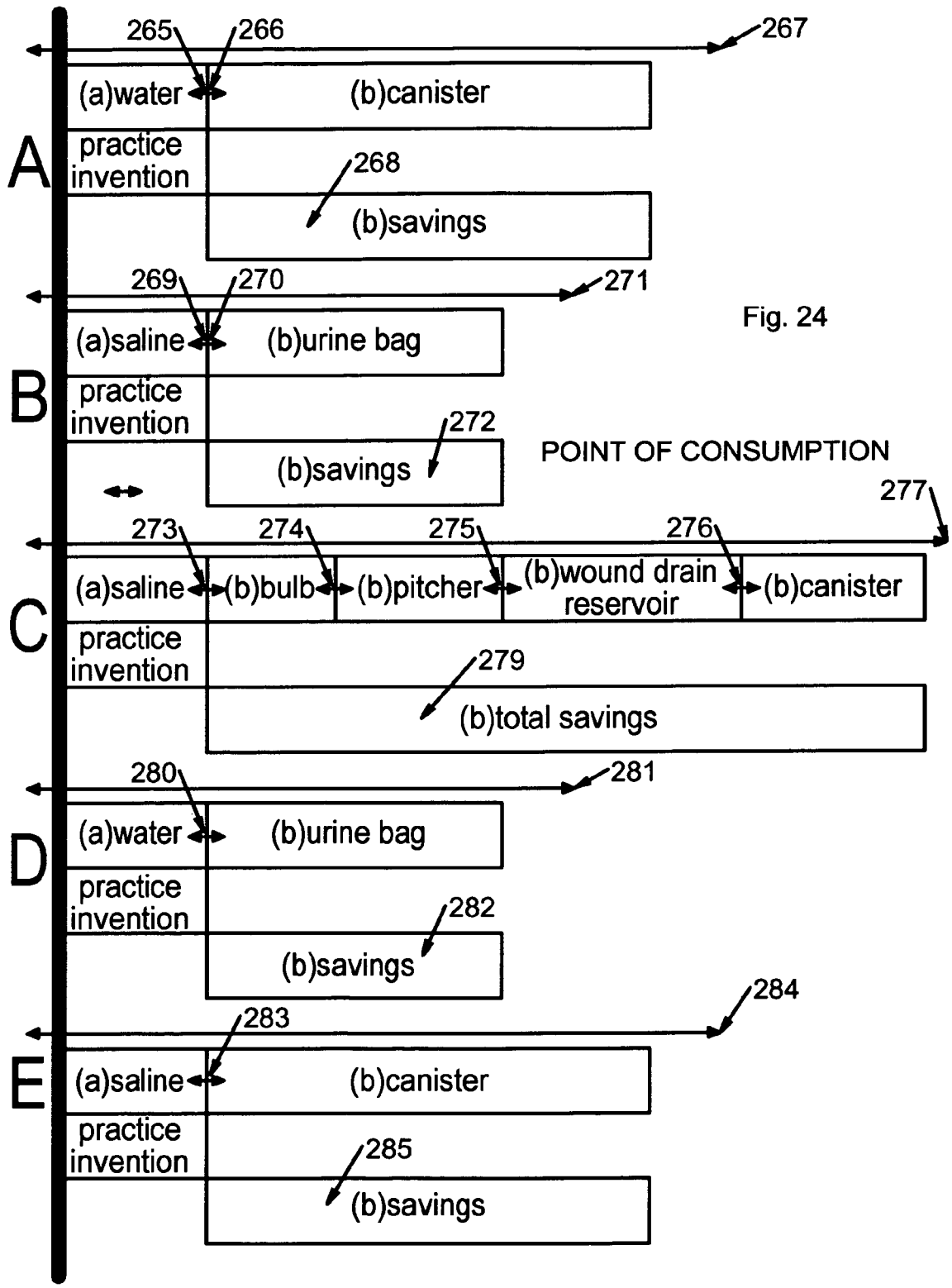
FIG. 24 shows a bar chart showing point of consumption expansion in examples A, B, C, D & E. A sterile liquid package has consumption value post egress of the initial sterile liquid as distributed and is depicted by the arrows showing the expanded points of consumption by ingressing and or ingressing and egressing of fluent materials as/from a source(s), as/from an origin(s) and/or as/from delivery destination(s).
Figure 25:
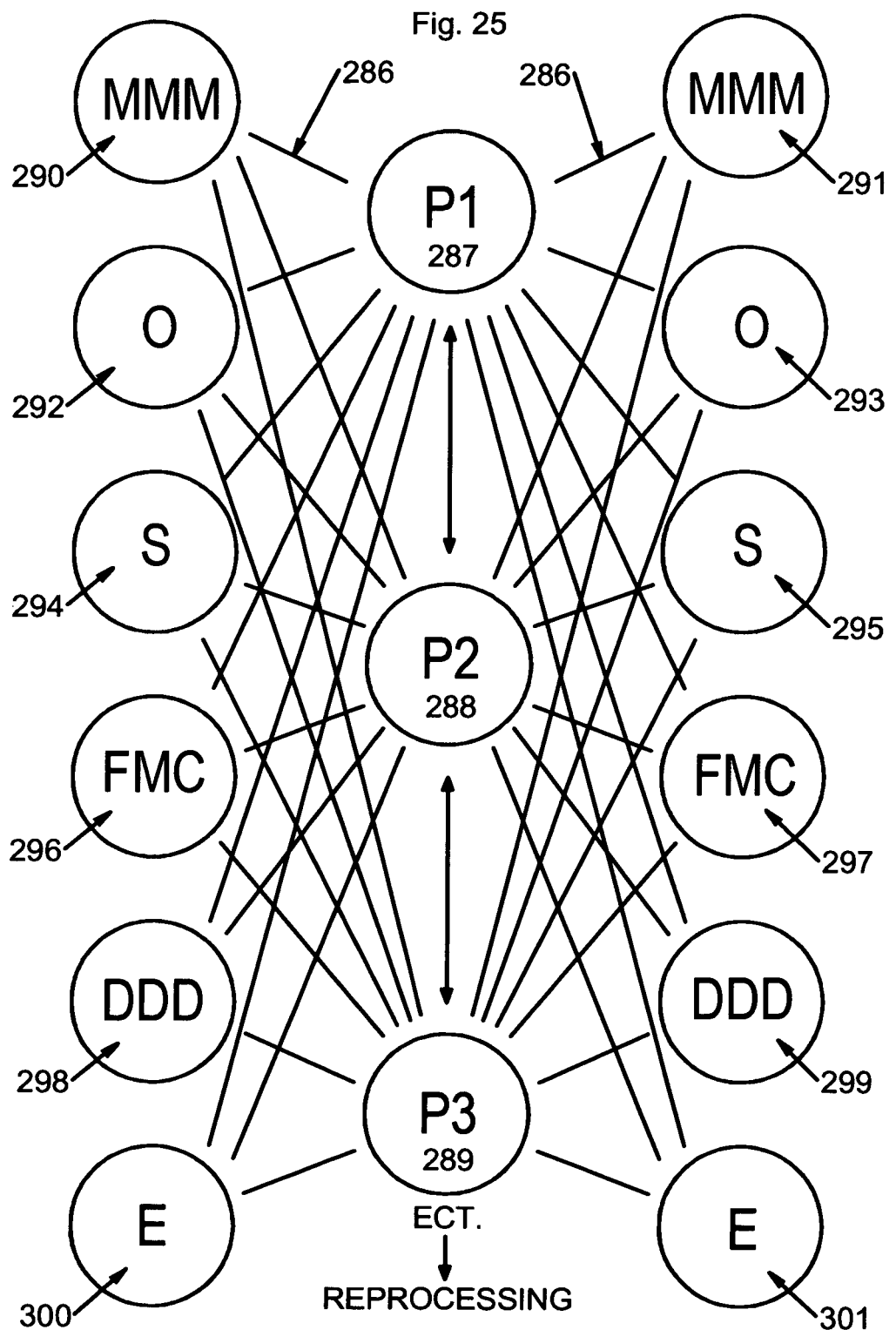

PATENT NO.          : 8,894,623 B2
APPLICATION NO.     : 12/932104
DATED               : November 25, 2014
INVENTOR(S)         : Romano It is certified that error appears in the above-identified patent and that said Letters Patent is hereby corrected as shown below:

In the specification
Column 2, line 65: delete "plow" and insert --flow-- to read "the flow pattern....".
Column 4, line 53: delete "of" and insert --or-- to read "one or more....".
Column 6, line 8: delete "from" and insert --for-- to read "ports for ingress....".
Column 6, line 17: delete "reduce" and insert --reduced-- to read "a reduced number....".
Column 6, line 58: delete "and" and insert --an-- to read "shows an embodiment....".
Column 7, line 16: delete "show" and insert --shows-- to read "FIG. 4 shows a....".
Column 7, line 37: delete "show" and insert --shown-- to read "is shown with....".
Column 7, line 52: delete "and" and insert --an-- to read "shows an embodiment....".
Column 8, line 57: delete "wholes" and insert --holes-- to read "the holes for....".
Column 9, line 22: delete "sows" and insert --shows-- to read "FIG. 22 shows three....".
Column 9, line 24: delete "and" and insert --as-- to read "enclosure as a....".
Column 9, line 27: delete "a" and insert --A-- to read "schematic A are....".
Column 9, line 36: delete "manufacture" and insert --manufactured-- to read "structures manufactured for....".
Column 9, line 42: delete "and" and insert --an-- to read "as an origin....".
Column 10, line 37: delete "show" and insert --shown-- to read "are shown for....".
Column 10, line 42: delete "provisional" and insert --nonprovisional-- to read "this nonprovisional patent....".
Column 11, line 16: delete "make" and insert --made-- to read "also made of....".
Column 11, line 20: delete "of" and insert --or-- to read "stopcock or valve....".
Column 11, line 40: delete "show" and insert --shown-- to read "is shown to....".
Column 11, line 50-51: insert --be-- between --may-- and --used-- to read "may be used....".
Column 12, line 22: insert --on-- between --Mounted-- and --one-- to read "Mounted on one....".
Column 12, line 55: delete "position" and insert --positioned-- to read "and positioned to....".
Column 13, line 3: insert --to-- between --correspond-- and --width-- to read "correspond to width....".
Column 13, line 5: delete twice "one-196" and insert --1-196-- to read "width 1-196 of...." in both places.

Signed and Sealed this
Sixth Day of October, 2015

Michelle K. Lee
*Director of the United States Patent and Trademark Office*

Column 13, line 9: delete "l191" and insert --L-191-- to read "length L-191 of....".
Column 13, line 12: delete "f" and insert --of-- to read "and 13 of Figs. 1 & 2....".